US010327912B1

(12) United States Patent
Suddaby

(10) Patent No.: US 10,327,912 B1
(45) Date of Patent: Jun. 25, 2019

(54) EXPANDABLE INTERBODY SPINAL FUSION DEVICE CAPABLE OF BEING DEPLOYED ENDOSCOPICALLY

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 0 days.

(21) Appl. No.: 15/872,549

(22) Filed: Jan. 16, 2018

(51) Int. Cl.
*A61F 2/44* (2006.01)
*A61F 2/30* (2006.01)

(52) U.S. Cl.
CPC ............ *A61F 2/4455* (2013.01); *A61F 2/442* (2013.01); *A61F 2002/30329* (2013.01); *A61F 2002/30579* (2013.01)

(58) Field of Classification Search
CPC .................. A61F 2/4455; A61F 2/442; A61F 2002/30329; A61F 2002/30579
USPC ........................................... 623/17.15, 17.16
See application file for complete search history.

(56) References Cited

U.S. PATENT DOCUMENTS

| | | | |
|---|---|---|---|
| 5,390,683 A | 2/1995 | Pisharodi | |
| 6,039,761 A | 3/2000 | Li et al. | |
| 6,306,125 B1 | 10/2001 | Parker et al. | |
| 6,395,034 B1 | 5/2002 | Suddaby | |
| 6,582,431 B1 | 6/2003 | Ray | |
| 6,582,451 B1 | 6/2003 | Marucci et al. | |
| 6,837,850 B2 | 1/2005 | Suddaby | |
| 6,958,077 B2 | 10/2005 | Suddaby | |
| 6,969,405 B2 | 11/2005 | Suddaby | |
| 7,070,598 B2 | 7/2006 | Lim et al. | |
| 7,597,714 B2 | 10/2009 | Suddaby | |
| 8,062,375 B2 | 11/2011 | Glerum et al. | |
| 8,398,713 B2 | 3/2013 | Weiman | |
| 8,409,282 B2 | 4/2013 | Kim | |
| 8,435,298 B2 | 5/2013 | Weiman | |
| 8,491,654 B2 | 7/2013 | Frey et al. | |
| 8,491,659 B2 | 7/2013 | Weiman | |
| 8,608,647 B2 | 12/2013 | Durant et al. | |
| 8,632,590 B2 | 1/2014 | Cauthen, III et al. | |
| 8,632,595 B2 | 1/2014 | Weiman | |
| 8,771,277 B2 | 7/2014 | Zappacosta et al. | |
| 8,845,731 B2 | 9/2014 | Weiman | |
| 8,845,732 B2 | 9/2014 | Weiman | |

(Continued)

FOREIGN PATENT DOCUMENTS

| WO | 0101895 A1 | 1/2001 |
|---|---|---|
| WO | 2010103344 A1 | 9/2010 |

OTHER PUBLICATIONS

Sahara Al Expandable Stabilization System; Advertisement flyer; Available from K2M, Inc. Leesburg, Virginia; Published as early as Oct. 20, 2015.

*Primary Examiner* — Pedro Philogene
*Assistant Examiner* — David C Comstock
(74) *Attorney, Agent, or Firm* — Simpson & Simpson, PLLC

(57) ABSTRACT

An expandable interbody spinal fusion device, including a superior component an inferior component and an expansion mechanism. The expansion mechanism including a threaded rod, a threaded collar operatively arranged to engage with the threaded rod and axially translate in a first axial direction, a fixed collar secured about the threaded rod, a first arm pivotably secured to the fixed collar, and a first strut pivotably secured to the first arm and the threaded collar.

20 Claims, 14 Drawing Sheets

(56) References Cited

U.S. PATENT DOCUMENTS

| | | |
|---|---|---|
| 8,845,734 B2 | 9/2014 | Weiman |
| 8,852,279 B2 | 10/2014 | Weiman |
| 8,864,833 B2 | 10/2014 | Glerum et al. |
| 8,920,506 B2 | 12/2014 | McGuckin, Jr. |
| 8,998,992 B2 | 4/2015 | Seifert et al. |
| 9,044,334 B2 | 6/2015 | Siegal et al. |
| 9,119,726 B2* | 9/2015 | Wei .................. A61F 2/442 |
| 9,622,872 B2 | 4/2017 | McKay |
| 9,889,019 B2 | 2/2018 | Rogers et al. |
| 2008/0114367 A1* | 5/2008 | Meyer .................. A61B 17/025 606/90 |
| 2009/0281628 A1 | 11/2009 | Oglaza et al. |
| 2010/0145396 A1 | 6/2010 | Thornes |
| 2011/0202135 A1 | 8/2011 | Baek et al. |
| 2013/0030533 A1 | 1/2013 | McGuckin, Jr. |
| 2013/0110239 A1 | 5/2013 | Siegal et al. |
| 2013/0178939 A1 | 7/2013 | Poulos |
| 2014/0379086 A1 | 12/2014 | Elahinia et al. |
| 2017/0209282 A1* | 7/2017 | Aghayev .............. A61F 2/4455 |
| 2018/0116818 A1 | 5/2018 | Rogers et al. |
| 2018/0303626 A1 | 10/2018 | Rogers et al. |

\* cited by examiner

EXPANDABLE INTERBODY SPINAL FUSION DEVICE CAPABLE OF BEING DEPLOYED ENDOSCOPICALLY

FIELD

The disclosure relates to spinal surgery, more particularly to intervertebral prosthesis, and, even more specifically, to a minimally invasive expandable interbody spinal fusion device capable of being deployed endoscopically.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae (C1-C7) form the neck, support the head and neck, and allow nodding and shaking of the head. The thoracic vertebrae (T1-T12) join with the ribs to form the rib cage. The five lumbar vertebrae (L1-L5) carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal, or neuro canal. The spinal cord and spinal nerves pass through the spinal canal, which protects them from injury. The spinal cord is the major column of nerve tissue that is connected to the brain and serves as an information superhighway between the brain and the body. The nerves in the spinal cord branch off to form pairs of nerve roots that travel through the small openings between the vertebrae and the intervertebral foramens.

The repetitive forces which act on these intervertebral discs during repetitive day-to-day activities of bending, lifting and twisting cause them to break down or degenerate over time. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and chemical irritation of surrounding neural elements cause pain, attended by varying degrees of disability. In addition, loss of disc space height relaxes tension on the longitudinal ligaments, thereby contributing to varying degrees of spinal instability such as spinal curvature.

Neural irritation and instability resulting from severe disc damage has been treated by removing the damaged disc and fusing adjacent vertebral elements. Removal of the disc relieves the mechanical and chemical irritation of neural elements, while osseous union solves the problem of instability. For example, in one surgical procedure, known as a discectomy (or diskectomy) with interbody fusion, the surgeon removes the nucleus of the disk and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, but with vertebra L3 in place atop disc $D_{L3-L4}$.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union.

Intervertebral prosthesis in various forms have therefore been used to provide immediate stability and to protect and preserve an environment that fosters growth of grafted bone such that a structurally significant bony fusion can occur.

Limitations of most present-day intervertebral implants are significant and revolve largely around marked variation in the disc space height and shape that results from either biologic variability or pathologic change. For example, if a disc space is 20 mm in height, a circular implant bridging this gap requires a minimum diameter of 20 mm just to contact the endplate of the vertebral bone. Generally, end plate disruption must occur to allow a generous bony union, meaning that an additional 2-3 mm must be added on either side resulting in a final implant size of 24-26 mm. During implantation from an anterior approach (from the front of the body), excessive retraction (pulling) is often required on the great blood vessels which greatly enhances the risk of devastating complication such as vascular tears or thrombosis. On the other hand, during a posterior approach, large implant diameters may require excessive traction on neural elements for adequate placement, even if all posterior bony elements are removed. In some instances, and adequate implant size cannot be inserted posteriorly, particularly if there is a significant degree of distraction to obtain stability by tautening the annular ligamentous tension band. Compromising implant size risks sub-optimal stability or a loose implant, both of which create a greater risk of migration within, or expulsion from, the disc space.

While expandable interbody fusion devices are being increasingly employed in interbody fusion, because of the desire to use minimally invasive fusion techniques, few have reached the capacity or capability of being deployed down the working channel of an endoscope or endoscopic access tube and therefore have not adequately achieved the ability to participate in true minimally invasive surgery.

Thus, there is a long-felt need for a minimally invasive expandable interbody spinal fusion device capable of easily being deployed endoscopically.

SUMMARY

According to aspects illustrated herein, there is provided an expandable interbody spinal fusion device, including a superior component an inferior component and an expansion mechanism. The expansion mechanism includes a threaded rod, a threaded collar operatively arranged to engage with the threaded rod and axially translate in a first axial direction, a fixed collar secured about the threaded rod, a first arm pivotably secured to the fixed collar, and a first strut pivotably secured to the first arm and the threaded collar.

According to aspects illustrated herein, there is provided an expandable interbody spinal fusion device, including a superior component, an inferior component and a first expansion mechanism. The first expansion mechanism includes a threaded rod, a superior plate, an inferior plate, a first threaded collar operatively arranged to engage with the threaded rod, a first fixed collar fixedly arranged about the threaded rod, a first arm pivotably secured to the superior plate and the first fixed collar, a first strut pivotably secured to the first arm and the first threaded collar, a second arm pivotably secured to the inferior plate the first fixed collar, and a second strut pivotably secured to the second arm and the first threaded collar, wherein the threaded rod is rotated about a first axis of rotation in a first rotational direction to displace the superior component in a first direction orthogonal to the first axis of rotation.

According to aspects illustrated herein, there is provided an expandable interbody spinal fusion device, including a superior component, an inferior component, and an expansion mechanism. The expansion mechanism includes a superior plate, an inferior plate, a threaded rod a first threaded collar operatively arranged to engage with the threaded rod, a second threaded collar operatively arranged to engage with the threaded rod, a fixed collar arranged about the threaded rod, a first arm pivotably secured to the superior plate and the fixed collar, a first strut pivotably secured to the first arm and the first threaded collar, a second arm pivotably secured to the inferior plate and the fixed collar, a second strut pivotably secured to the second arm and the first threaded collar, a third arm pivotably secured to the superior plate and the fixed collar, a third strut pivotably secured to the third arm and the second threaded collar, a fourth arm pivotably secured to the inferior plate and the fixed collar, and a fourth strut pivotably secured to the fourth arm and the second threaded collar, wherein the threaded rod is rotated in a first rotational direction about an axis of rotation to displace the first threaded collar in a first axial direction and displace the second threaded collar in a second axial direction, and displacing the superior component in a first radial direction orthogonal to the first axial direction, and displace the inferior component in a second radial direction orthogonal to the first axial direction and opposite the first radial direction.

These, and other objects and advantages, will be readily appreciable from the following description of preferred embodiments and from the accompanying drawings and claims.

BRIEF DESCRIPTION OF THE SEVERAL VIEWS OF THE DRAWINGS

The nature and mode of operation of the present disclosure will now be more fully described in the following detailed description of the embodiments taken with the accompanying figures, in which.

DETAILED DESCRIPTION OF EMBODIMENTS

At the outset, it should be appreciated that like drawing numbers on different drawing views identify identical, or functionally similar, structural elements. While the embodiments are described with respect to what is presently considered to be the preferred aspects, it is to be understood that the invention as claimed is not limited to the disclosed aspect. The present invention is intended to include various modifications and equivalent arrangements within the spirit and scope of the appended claims.

The term "Superior Component" as used in the present disclosure is intended to mean the component of the body of the implant located in the highest position relative to the other components in first radial direction RD1.

The term "Inferior Component" as used in the present disclosure is intended to mean the component of the body of the implant located in the lowest position relative to the other components in first radial direction RD1.

Moreover, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Furthermore, it is understood that this disclosure is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
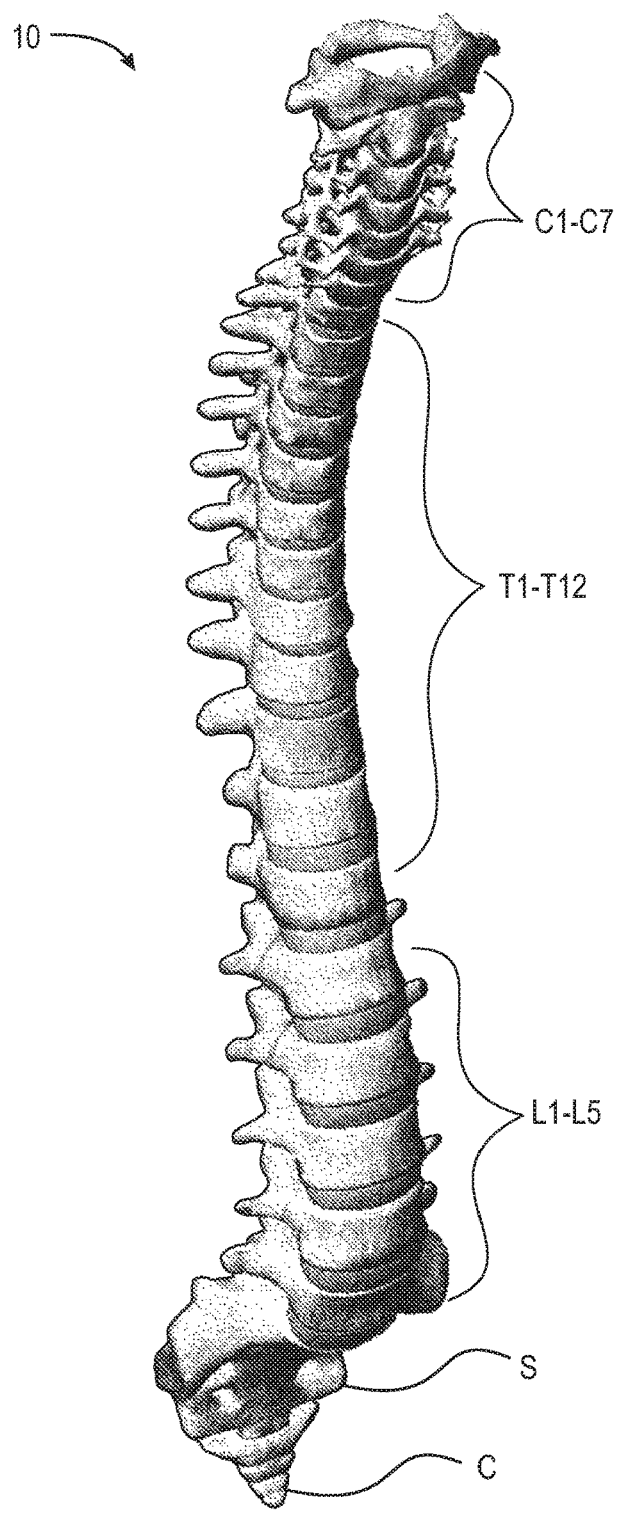
FIG. 1 is an anterior perspective view of spinal column 10.
Figure 2:
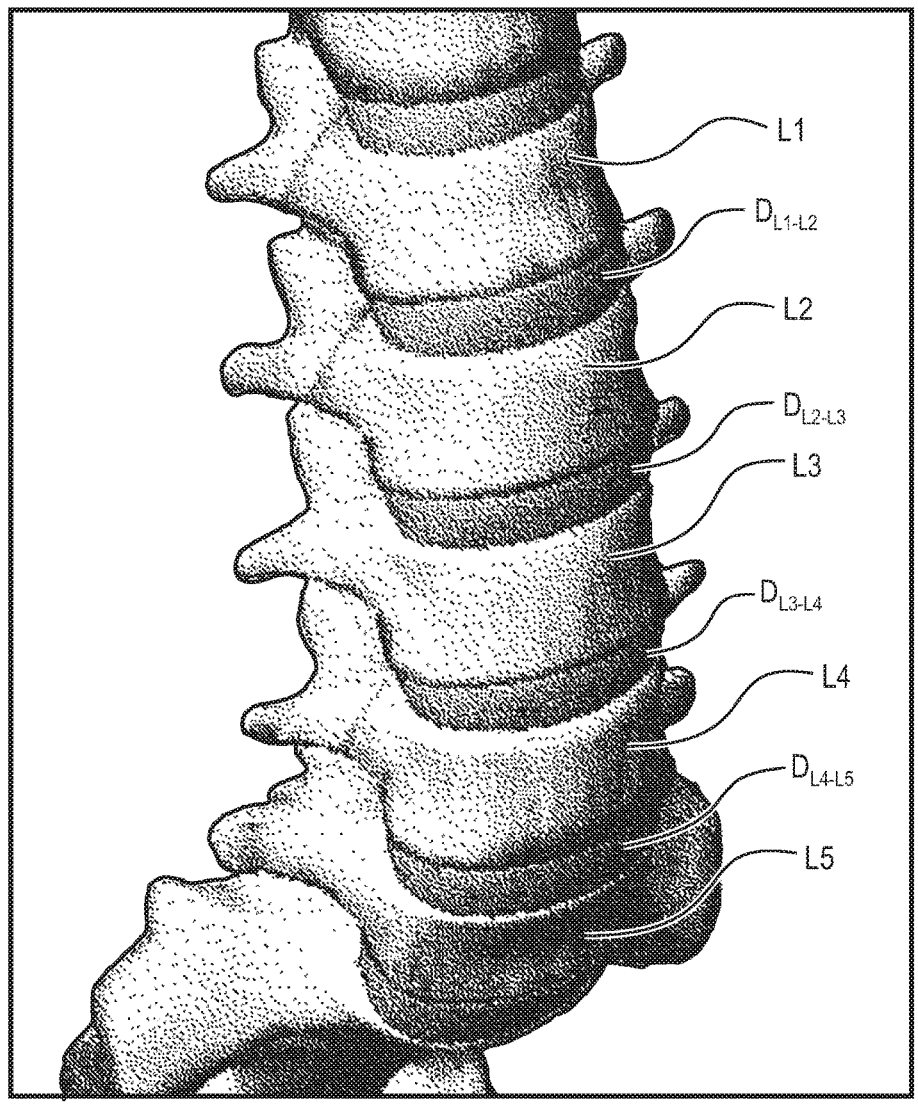
FIG. 2 is an anterior perspective view of the lumbar section of spinal column 10.
Figure 3:
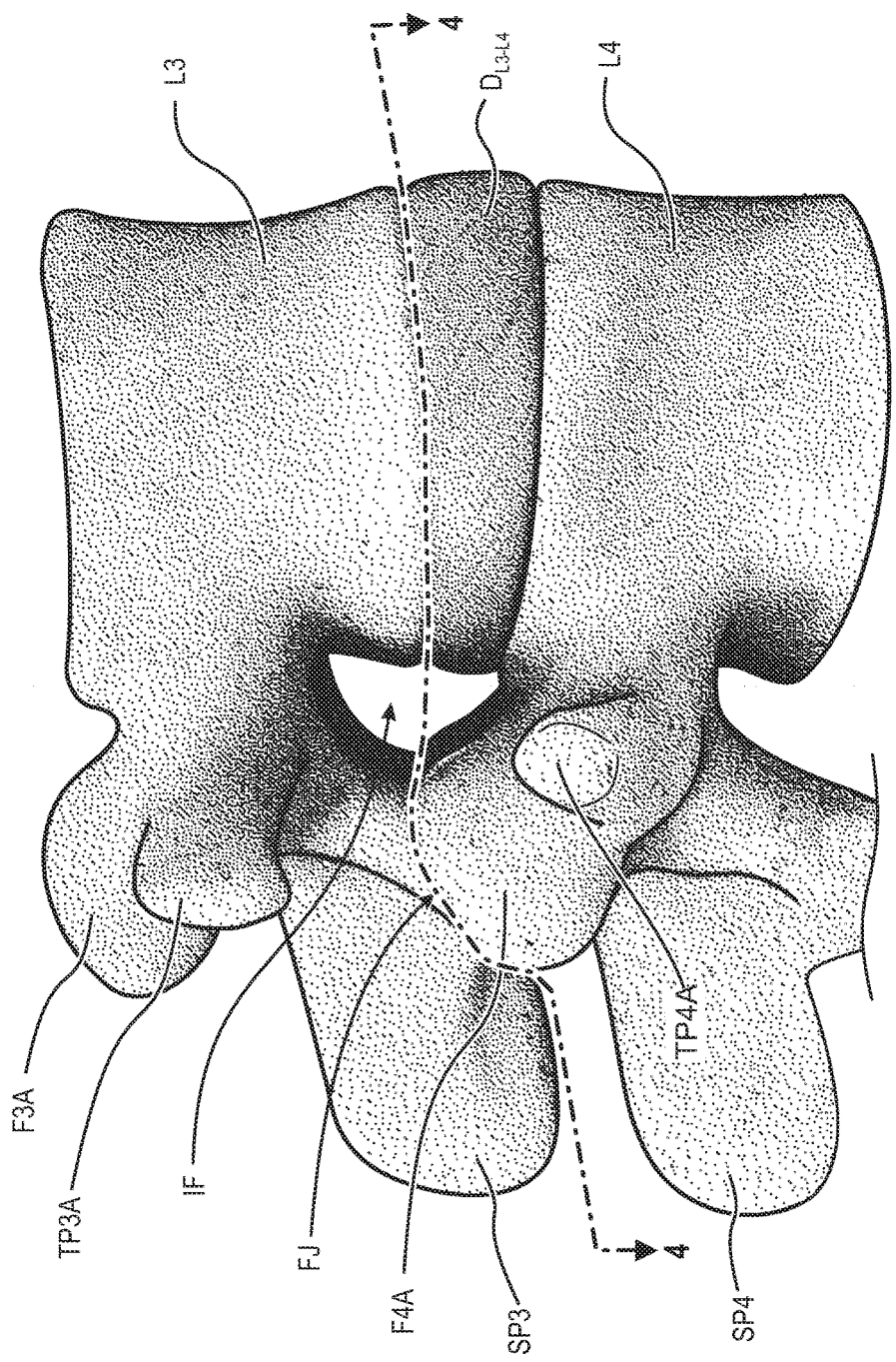
FIG. 3 is a lateral perspective view of L3, L4 vertebrae and disc $D_{L3-L4}$ and related spinal anatomy.
Figure 4:
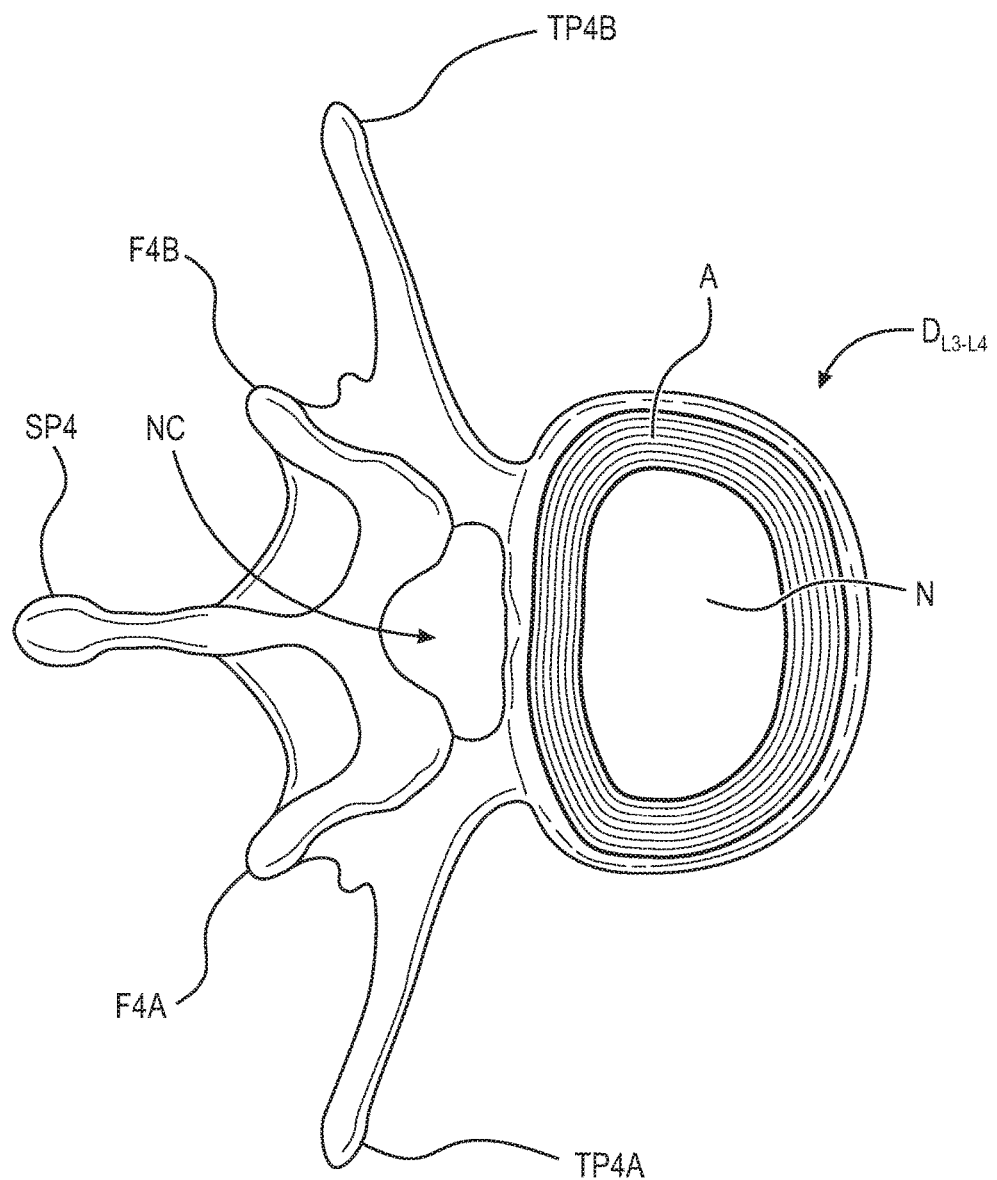
FIG. 4 is a top view of a section of the spinal column, taken generally along line 4-4 in FIG. 3.
Figure 5:
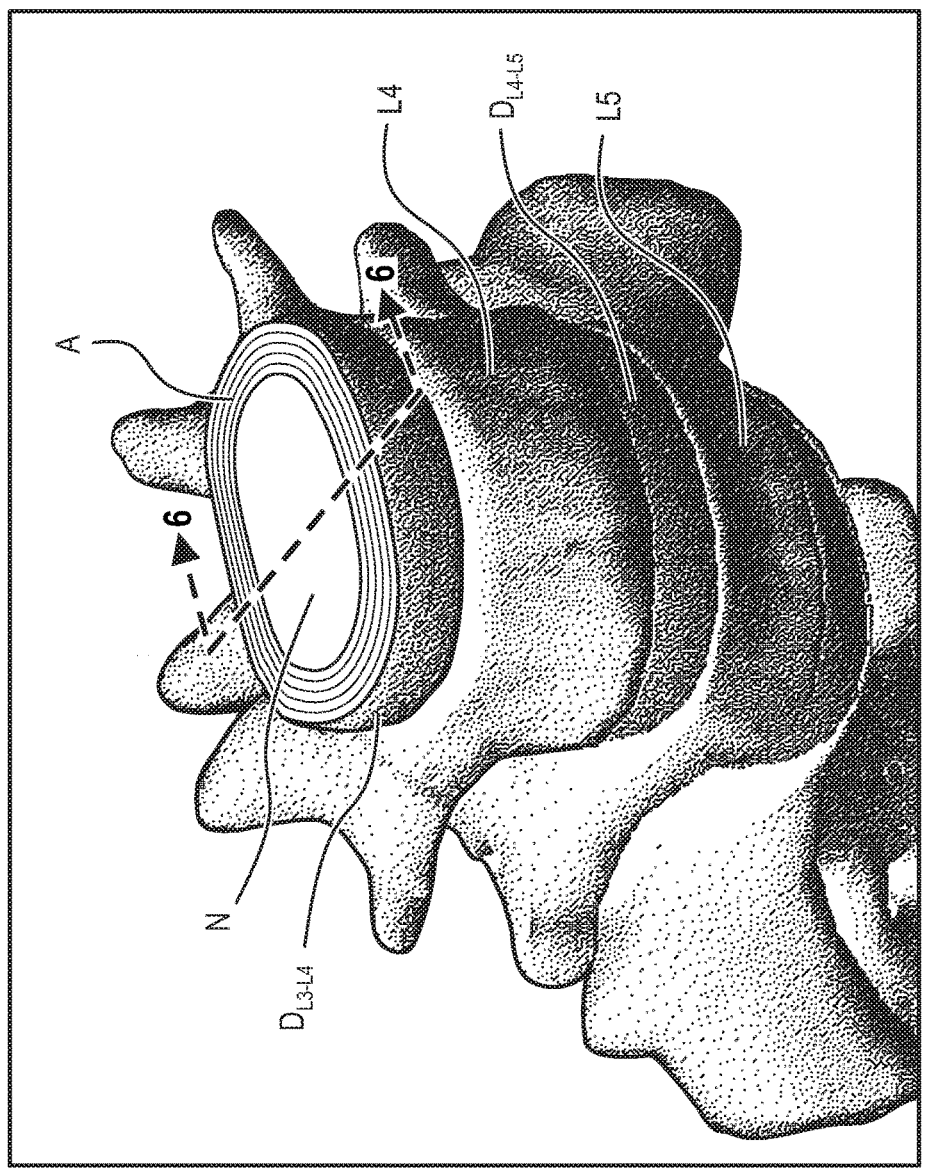
FIG. 5 is an enlarged anterior perspective view of the spinal column shown in FIG. 2, except with vertebra L3 and all other structure above L3 removed.
Figure 6:
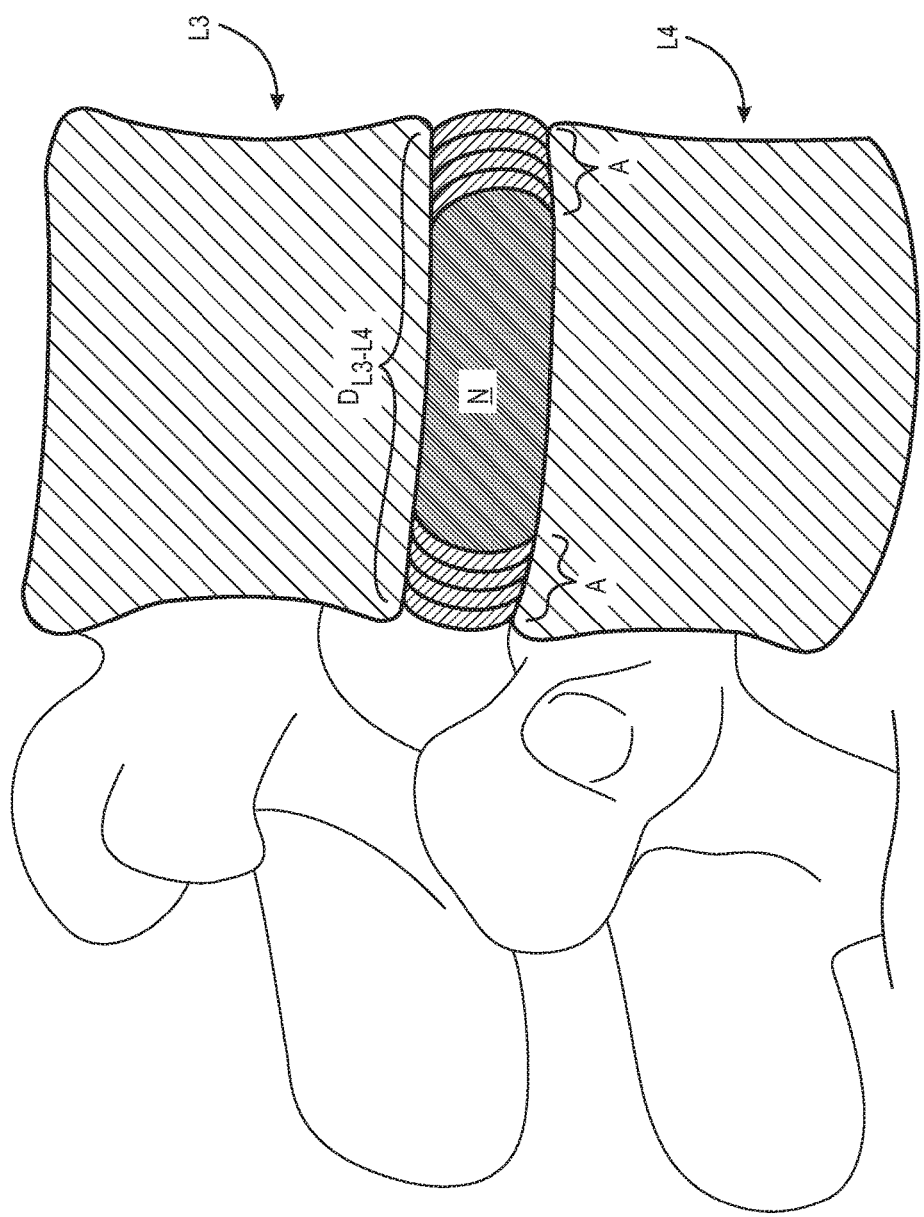
FIG. 6 is a partial cross-sectional view of the L4 vertebra and $D_{L3-L4}$ disc shown in FIG. 5, including L3 in cross-section.
Figure 7:
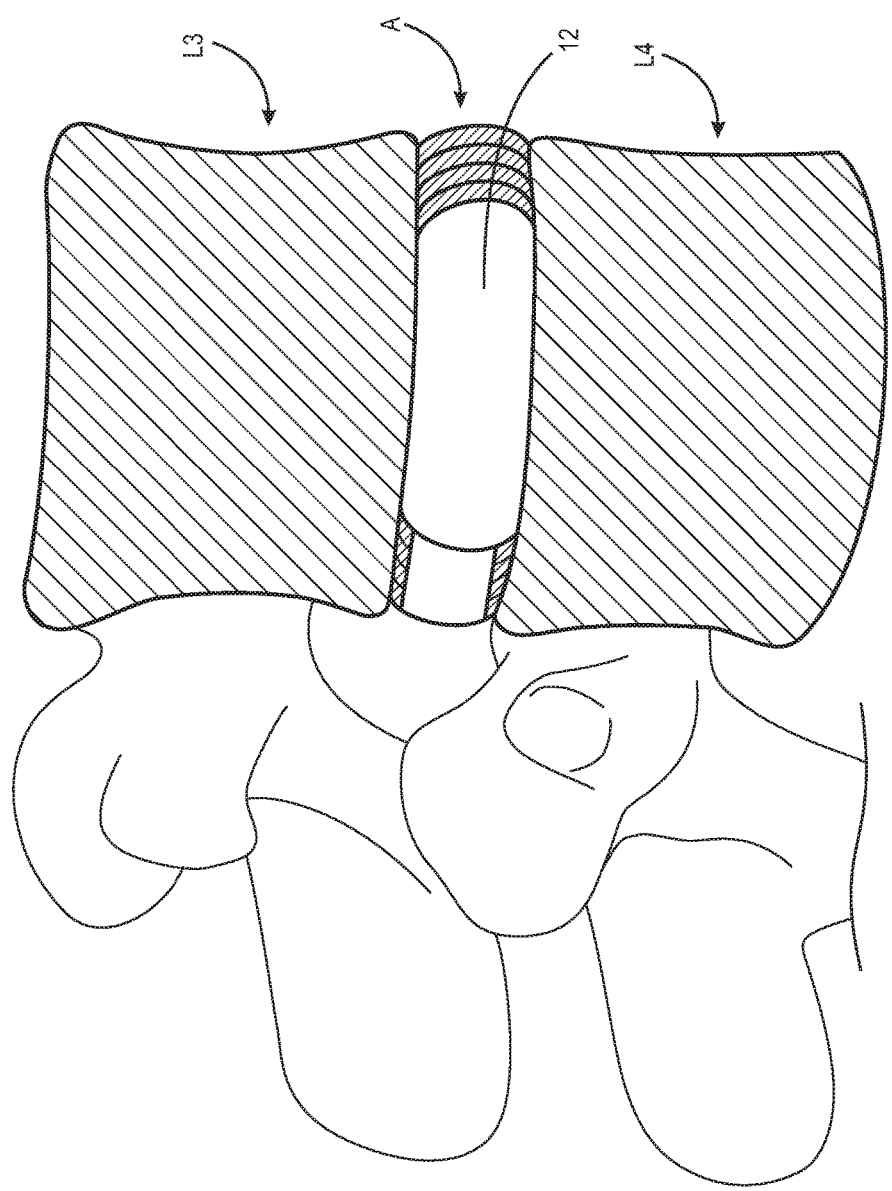
FIG. 7 is a partial cross-sectional view of the L4 vertebra and $D_{L3-L4}$ disc shown in FIG. 5, showing the removal of the disc nucleus post-discectomy.

Adverting now to the Figures, and as described previously, FIGS. 1-6 depict various parts and sections of spinal anatomy. FIG. 7 illustrates a partial cross-sectional view of the L3 and L4 vertebra with disc $D_{L3-L4}$ removed (post discectomy) able to receive expandable interbody spinal fusion device 100.

Figure 8:
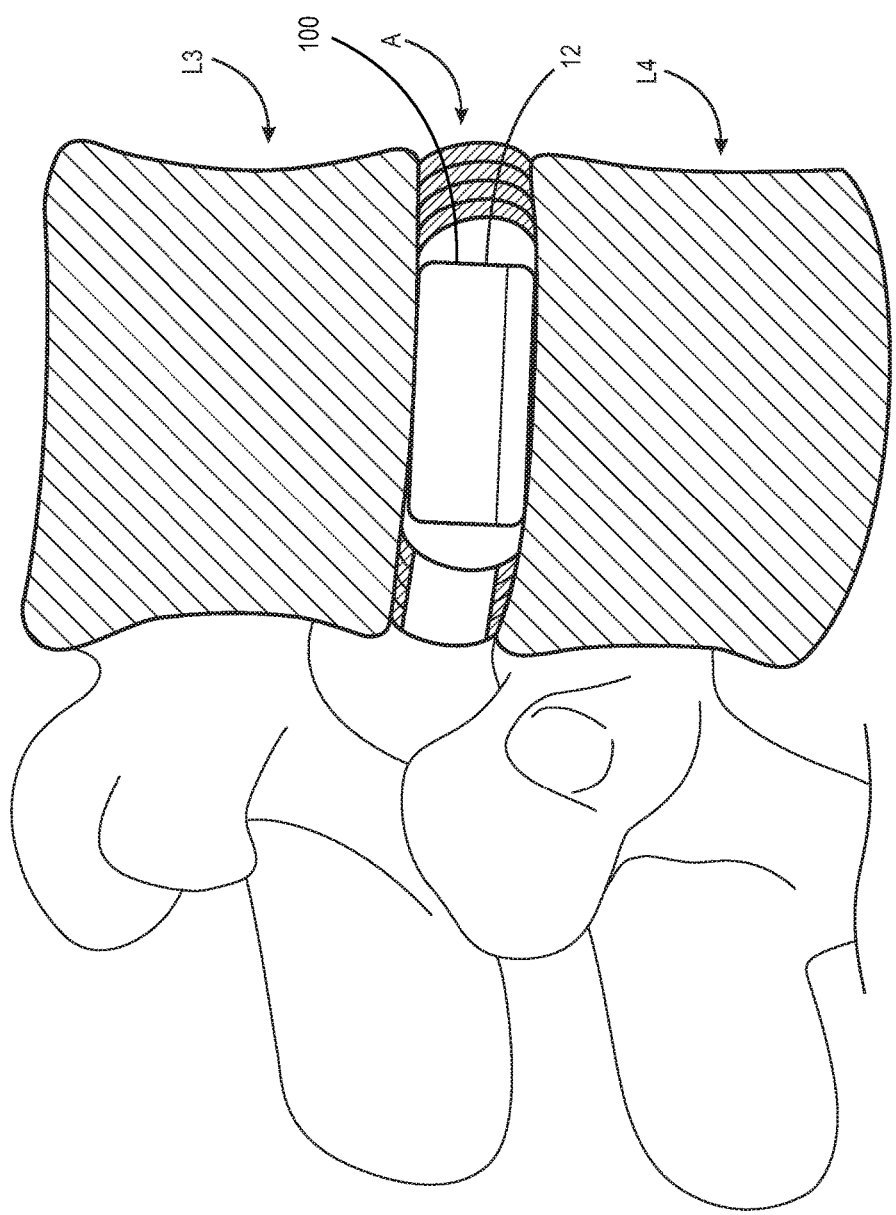
FIG. 8 illustrates the introduction of an expandable interbody spinal fusion device into the disc space in an unexpanded state.

FIG. 8 illustrates a partial cross-sectional view of the L3 and L4 vertebra with expandable interbody spinal fusion device 100 in place within disc space 12 in an unexpanded state.

Figure 9:
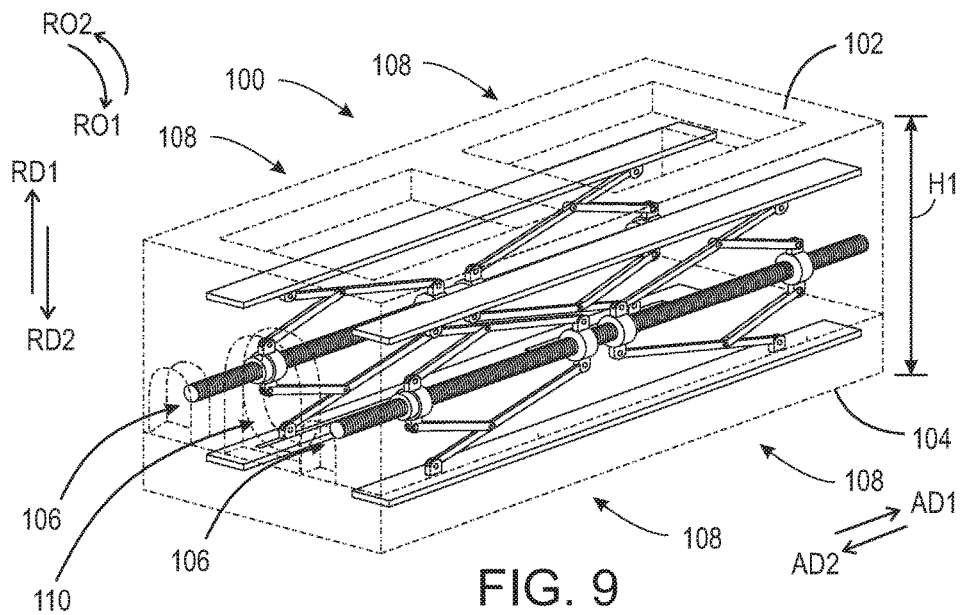
FIG. 9 is a perspective view of an expandable interbody spinal fusion device with a first example embodiment of expansion mechanisms in position therein, in a collapsed state.

FIG. 9 is a perspective view of expandable interbody spinal fusion device 100 with expansion mechanisms 106 (discussed infra) in position therein, in a collapsed state. Device 100 comprises superior component 102, inferior component 104, and expansion mechanisms 106 arranged to displace superior component 102 in a first radial direction RD1 relative to inferior component 104 giving device 100 an expanded height $H_2$ (shown in FIG. 10) greater than unexpanded height $H_1$. Superior component 102 and inferior component 104 further comprise at least one first aperture 108 arranged to allow fusion between bone fusing material and the adjacent vertebra, and a second aperture 110 is located on the front face of device 100 and arranged to allow the introduction of bone fusing material into device 100 during surgery. Second aperture 110 is illustrated as an arched slot as a non-limiting example, however, it should be appreciated that second aperture 110 could be any suitable aperture that would allow for the introduction of bone fusing material into device 100.

Figure 10:
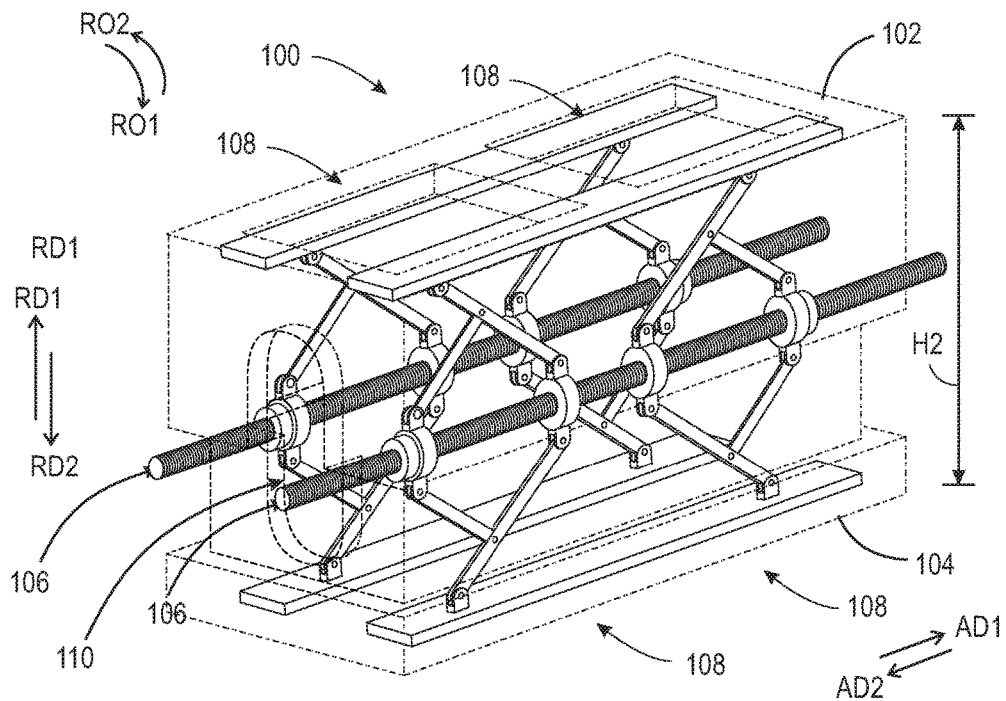
FIG. 10 is a perspective view of an expandable interbody spinal fusion device with a first example embodiment of expansion mechanisms in position therein, in an expanded state.

FIG. 10 is a perspective view of expandable interbody spinal fusion device 100 with expansion mechanisms 106 in position therein, in an expanded state. During surgery and after device 100 is implanted in disc space 12, a surgeon can apply torque to expansion mechanisms 106 via any device that imparts rotational force upon expansion mechanisms 106 (e.g., a screw driver or impact driver). Although not illustrated, various means to engage a screw driver or impact driver can be affixed to either end of rod 116 (discussed infra) of expansion mechanisms 106, e.g., the rod could have an embedded cavity having the shape of various screw heads known in the art, or an additional physical member having any of the various screw heads known in the art could be affixed to rod 116. This rotational force causes expansion mechanisms 106 to displace superior component 102 in radial direction RD1 relative to inferior component 104 giving device 100 an expanded height $H_2$, greater than $H_1$. It should be appreciated that expansion mechanisms 106 can be expanded to any height between unexpanded height $H_1$ and expanded height $H_2$. Although device 100 is illustrated with expansion mechanisms 106 disposed therein, it should be appreciated that device 100 can also include other expansion mechanisms e.g., expansion mechanisms 206 and 306 discussed infra, and any combination of these expansion mechanisms therein.

Figure 11:
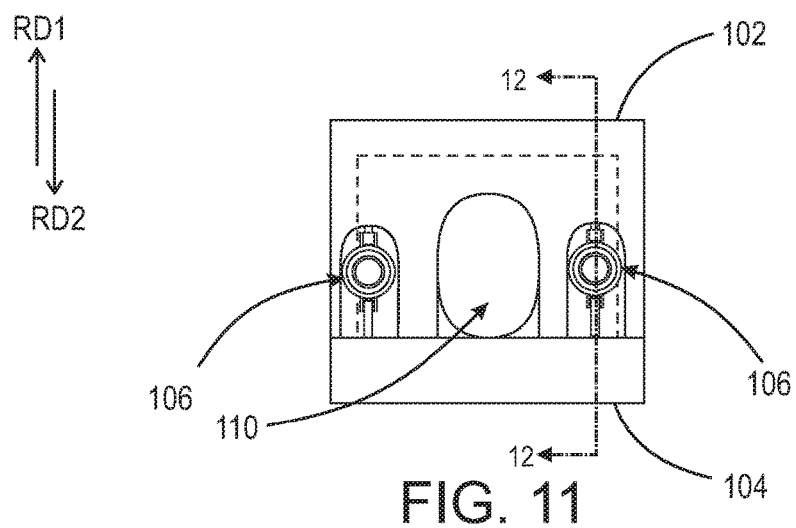
FIG. 11 is a front elevational view of an expandable interbody spinal fusion device with a first example embodiment of expansion mechanisms in position therein, in a collapsed state.
Figure 12:
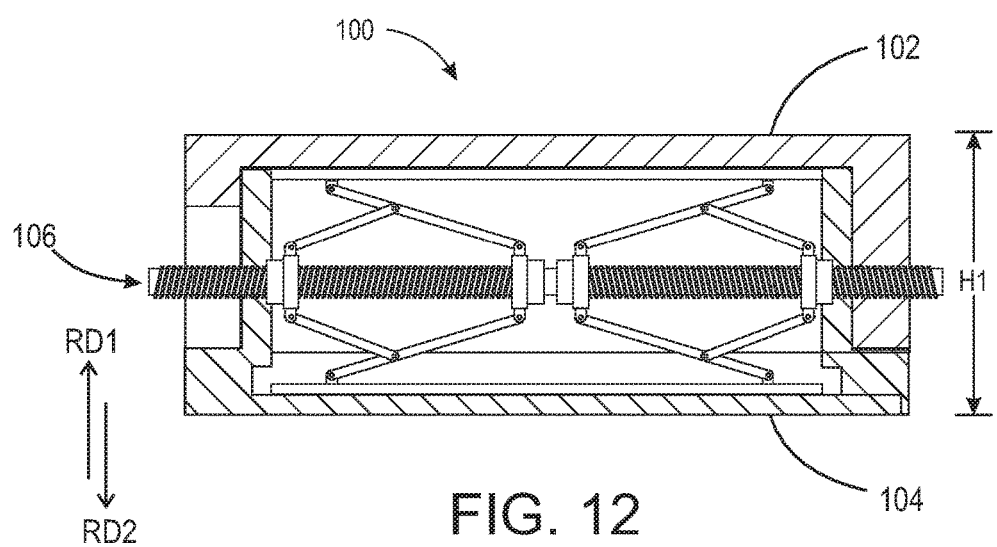
FIG. 12 is a cross-sectional view of an expandable interbody spinal fusion device taken generally along line 12-12 in FIG. 11 with a first example embodiment of expansion mechanisms in position therein, in a collapsed state.

FIG. 11 is a front elevational view of expandable interbody spinal fusion device 100 with expansion mechanisms 106 in position therein, in a collapsed state. FIG. 12 is a cross-sectional view of expandable interbody spinal fusion device 100, taken generally along line 12-12 in FIG. 11 with expansion mechanisms 106 in position therein, in a collapsed state.

Figure 13:
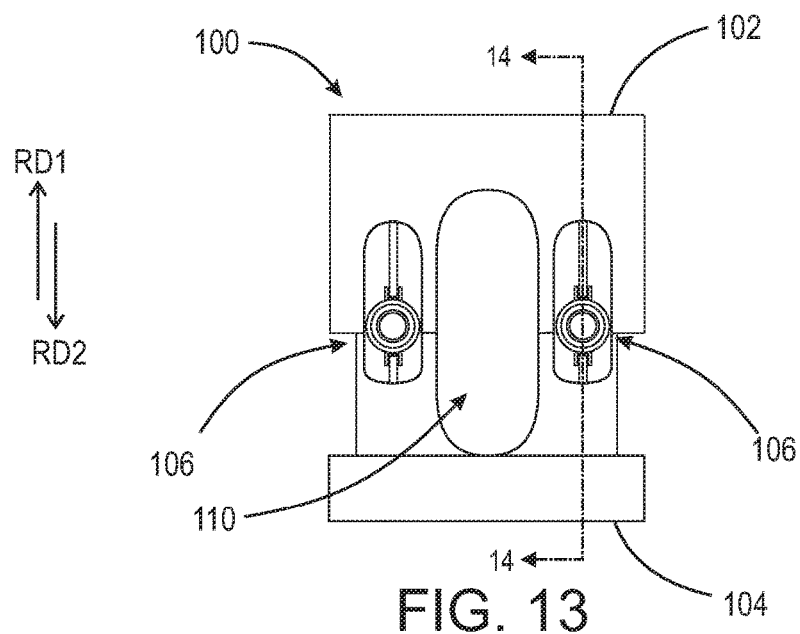
FIG. 13 is a front elevational view of an expandable interbody spinal fusion device with a first example embodiment of expansion mechanisms in position therein, in an expanded state.
Figure 14:
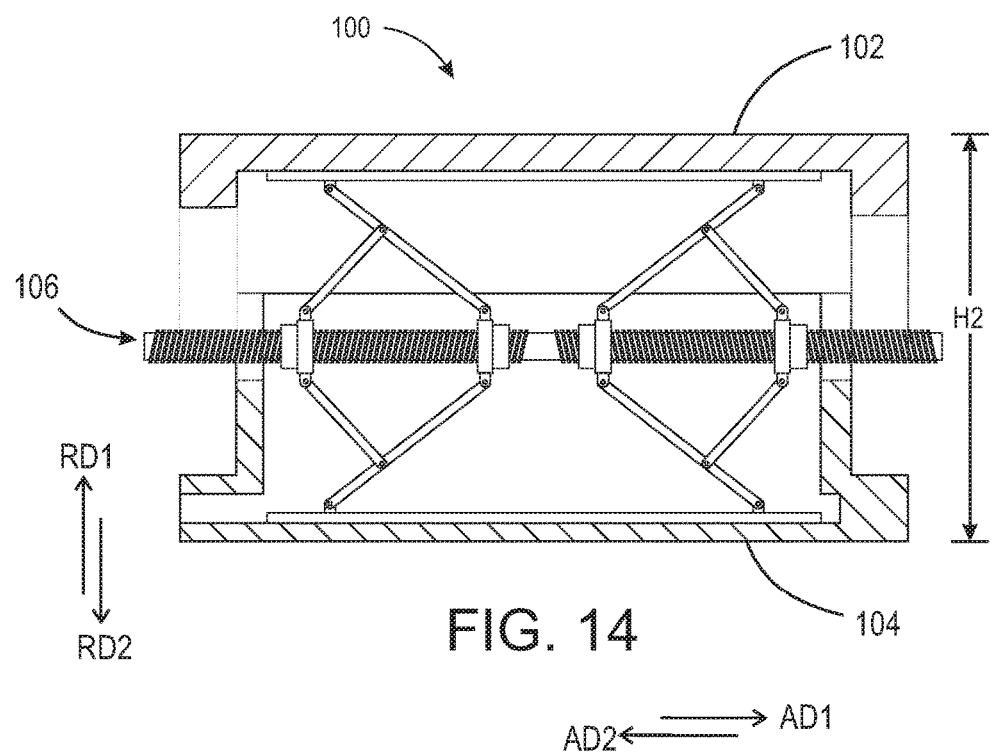
FIG. 14 is a cross-sectional view of an expandable interbody spinal fusion device taken generally along line 14-14 in FIG. 13 with a first example embodiment of expansion mechanisms in position therein, in an expanded state.

FIG. 13 is a front elevational view of expandable interbody spinal fusion device 100 with expansion mechanisms 106 in position therein, in an expanded state. FIG. 14 is a cross-sectional view of expandable interbody spinal fusion device 100 taken generally along line 14-14 in FIG. 13 with expansion mechanisms 106 in position therein, in an expanded state.

Figure 15:
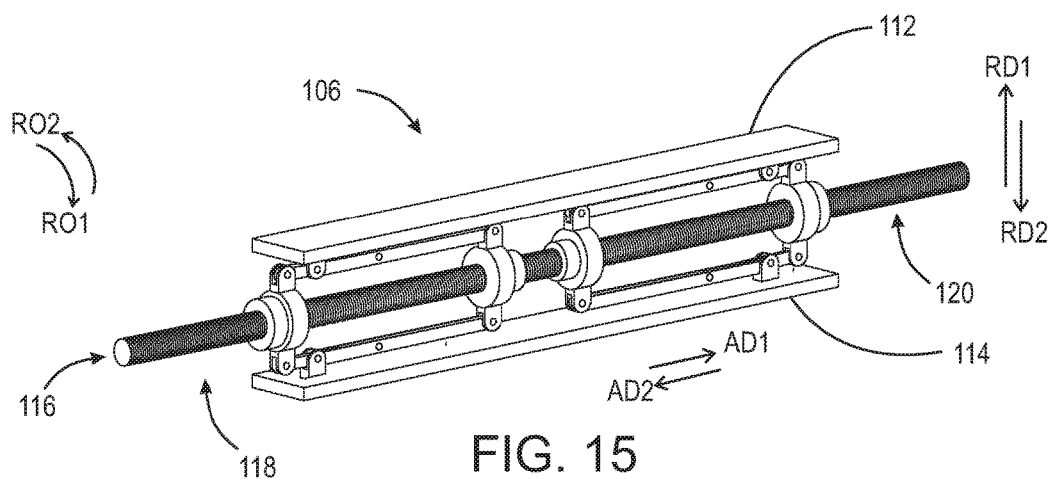
FIG. 15 is a perspective view of a first example embodiment of an expansion mechanism in a collapsed state.
Figure 16:
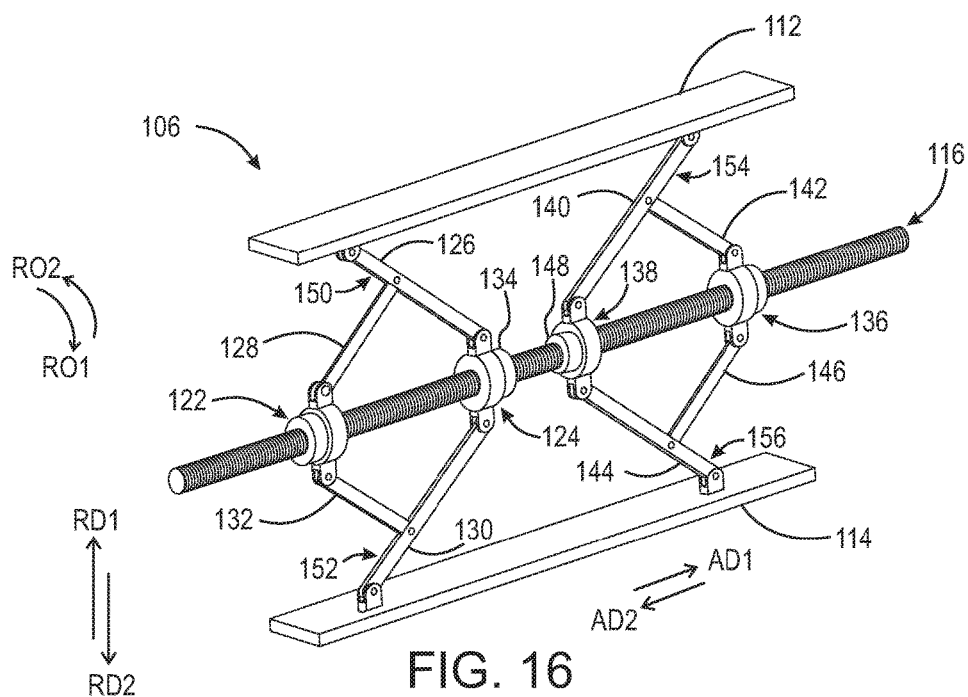
FIG. 16 is a perspective view of a first example embodiment of an expansion mechanism in an expanded state.

FIGS. 15 and 16 illustrate perspective views of expansion mechanism 106 in a collapsed and expanded state, respectively. Expansion mechanism 106 includes superior plate 112, inferior plate 114, threaded rod 116 having first end 118 and second end 120, first threaded collar 122, first fixed collar 124, first arm 126, first strut 128, second arm 130, second strut 132, and locking mechanism 134. Superior plate 112 and inferior plate 114 are substantially planar members spanning a substantial portion of the length of device 100 when in place therein. Superior plate 112 and inferior plate 114 are arranged to contact and engage with the inner surface of superior component 102 and inferior component 104 of device 100, respectively. Threaded rod 116 is arranged to run along the length of device 100 and to rotate within device 100 in either first rotational direction RO1 or second rotational direction RO2. Threaded rod 116 has an outer circumferential surface which contains helical threading. The helical threading can be threaded in first rotational direction RO1 and/or second rotational direction RO2.

First threaded collar 122 is a substantially toroidal member with inner threading operatively arranged to receive and engage with the helical threading on first end 118 of threaded rod 116. As threaded rod 116 is rotated in first rotational direction RO1 or second rotational direction RO2, the first threaded collar 122 translates about threaded rod 116 in first axial direction AD1 or second axial direction AD2, dependent on the direction of rotation of threaded rod 116. First fixed collar 124 is a substantially toroidal member arranged about threaded rod 116 and arranged to rotate freely in place and maintain position in first axial direction AD1. This free rotation can be accomplished by leaving the inner circumferential surface of first fixed collar 124 free of threading, such that the threading of threaded rod 116 cannot engage with and influence first fixed collar 124. Additionally, a locking mechanism, i.e., locking mechanism 134, discussed infra, can be used to prevent first fixed collar 124 from translating about threaded rod 116 in first axial direction AD1 and/or second axial direction AD2. Alternatively, and although not illustrated in the figures, the inner circumferential surface of first fixed collar 124 can contain an annular protrusion arranged to fit within, and slidingly engage with, a corresponding annular recess at a fixed axial position on the outer circumferential surface of threaded rod 116.

First arm 126 is pivotably connected between first fixed collar 124 and superior plate 112. One end of first arm 126 is pivotably connected to a protrusion on the inner surface of superior plate 112 which can comprise a pin arranged to allow first arm 126 to pivot with respect to superior plate 112. The other end of first arm 126 is pivotably connected to a protrusion on the outer circumferential surface of first fixed collar 124 which can comprise a pin arranged to allow first arm 126 to pivot with respect to first fixed collar 124. First strut 128 is pivotably connected between first threaded collar 122 and first arm 126. One end of first strut 128 is pivotably connected to a protrusion on the outer circumferential surface of first threaded collar 122 which can comprise a pin arranged to allow first strut 128 to pivot with respect to first threaded collar 122. The other end of first strut 128 is pivotably connected to first arm 126 which can comprise a pin arranged to allow first strut 128 to pivot with respect to first arm 126.

Second arm 130 is pivotably connected between first fixed collar 124 and inferior plate 114. One end of second arm 130 is pivotably connected to a protrusion on the inner surface of inferior plate 114 which can comprise a pin arranged to allow second arm 130 to pivot with respect to inferior plate 114. The other end of second arm 130 is pivotably connected to a second protrusion on the outer circumferential surface of first fixed collar 124 which can comprise a pin arranged to allow second arm 130 to pivot with respect to first fixed collar 124. Second strut 132 is pivotably connected between first threaded collar 122 and second arm 130. One end of second strut 132 is pivotably connected to a second protrusion on the outer circumferential surface of first threaded collar 122 which can comprise a pin arranged to allow second strut 132 to pivot with respect to first threaded collar 122. The other end of second strut 132 is pivotably connected to second arm 130 which can comprise a pin arranged to allow second strut 132 to pivot with respect to second arm 130.

Locking mechanism 134 is arranged about threaded rod 116 and can be positioned axially adjacent to first fixed collar 124 in the first axial direction AD1 and/or the second axial direction AD2. As first fixed collar 124 does not have internal threading, locking mechanism 134 prevents first fixed collar 124 from translating about threaded rod 116 in first axial direction AD1 and/or second axial direction AD2. In an example embodiment, locking mechanism 134 is a lock washer, a crimp ring retainer, or a serrated lock washer. However, it should be appreciated that locking mechanism 134 can be any mechanism suitable for preventing axial translation of fixed collar 124 about a rod.

During surgery, and after device 100 containing expansion mechanisms 106 is implanted in situ within disc space 12, a surgeon can apply torque to threaded rod 116 via any device that imparts rotational force (e.g., a screw driver or impact driver). As threaded rod 116 rotates in first rotational direction RO1, first fixed collar 124 maintains a fixed axial position about threaded rod 116 as it is confined by locking mechanism 134. Additionally, as threaded rod 116 rotates in first rotational direction RO1, the inner circumferential threading of first threaded collar 122 engages with the helical threading of threaded rod 116 causing first threaded collar 122 to translate in first axial direction AD1. The translational motion imparted to first threaded collar 122, in conjunction with the lack of translational motion of first fixed collar 124, imparts a force upon first strut 128 and second strut 132 which in turn impart a force upon first arm 126 and second arm 130 in first radial direction RD1 and second radial direction RD2, respectively.

Expansion mechanism 106 also includes second threaded collar 136, second fixed collar 138, third arm 140, third strut 142, fourth arm 144, fourth strut 146, and locking mechanism 148. Second threaded collar 136 is a substantially toroidal member with inner threading operatively arranged to receive and engage with the helical threading on second end 120 of threaded rod 116. As threaded rod 116 is rotated in first rotational direction RO1 or second rotational direction RO2, second threaded collar 136 translates about threaded rod 116 in first axial direction AD1 or second axial direction AD2, dependent on the direction of rotation of threaded rod 116. Second fixed collar 138 is a substantially toroidal member arranged about threaded rod 116 and arranged to rotate freely in place and maintain position in first axial direction AD1. This free rotation can be accomplished by leaving the inner circumferential surface of second fixed collar 138 free of threading, such that the threading of threaded rod 116 cannot engage with and influence second fixed collar 138. Additionally, a locking mechanism, i.e., locking mechanism 148, discussed infra, can be used to prevent second fixed collar 138 from translating about threaded rod 116 in first axial direction AD1 and/or second axial direction AD2. Alternatively, and although not illustrated in the figures, the inner circumferential surface of second fixed collar 138 can contain an annular protrusion arranged to fit within and slidingly engage with a corresponding annular recess at a fixed axial position on the outer circumferential surface of threaded rod 116.

Third arm 140 is pivotably connected between second fixed collar 138 and superior plate 112. One end of third arm 140 is pivotably connected to a protrusion on the inner surface of superior plate 112 which can comprise a pin arranged to allow third arm 140 to pivot with respect to superior plate 112. The other end of third arm 140 is pivotably connected to a protrusion on the outer circumferential surface of second fixed collar 138 which can comprise a pin arranged to allow third arm 140 to pivot with respect to second fixed collar 138. Third strut 142 is pivotably connected between second threaded collar 136 and third arm 140. One end of third strut 142 is pivotably connected to a protrusion on the outer circumferential surface of second threaded collar 136 which can comprise a pin arranged to allow third strut 142 to pivot with respect to second threaded collar 136. The other end of third strut 142 is pivotably connected to third arm 140 which can comprise a pin arranged to allow third strut 142 to pivot with respect to third arm 140.

Fourth arm 144 is pivotably connected between second fixed collar 138 and inferior plate 114. One end of fourth arm 144 is pivotably connected to a protrusion on the inner surface of inferior plate 114 which can comprise a pin arranged to allow fourth arm 144 to pivot with respect to inferior plate 114. The other end of fourth arm 144 is pivotably connected to a second protrusion on the outer circumferential surface of second fixed collar 138 which can comprise a pin arranged to allow fourth arm 144 to pivot with respect to second fixed collar 138. Fourth strut 146 is pivotably connected between second threaded collar 136 and fourth arm 144. One end of fourth strut 146 is pivotably connected to a second protrusion on the outer circumferential surface of second threaded collar 136 which can comprise a pin arranged to allow fourth strut 146 to pivot with respect to second threaded collar 136. The other end of fourth strut 146 is pivotably connected to fourth arm 144 which can comprise a pin arranged to allow fourth strut 146 to pivot with respect to fourth arm 144.

A second locking mechanism, i.e., locking mechanism 148 can be arranged about threaded rod 116 and be positioned axially adjacent to second fixed collar 138 in the first axial direction AD1 and/or the second axial direction AD2. As second fixed collar 138 does not have internal threading, locking mechanism 148 prevents second fixed collar 138 from translating about threaded rod 116 in first axial direction AD1 and/or second axial direction AD2. In an example embodiment, locking mechanism 148 is a lock washer, a crimp ring retainer, or a serrated lock washer. However, it should be appreciated that locking mechanism 148 can be any mechanism suitable for preventing axial translation about a rod. It should be appreciated that the opposing movement of first threaded collar 122 and second threaded collar 136 can be achieved by having opposing threading on their respective inner circumferential surfaces (as can be seen in FIGS. 12 and 14), or the threaded collars could have identical threading and first end 118 of threaded rod 116 could comprise helical threading of a first direction while second end 120 of threaded rod 116 could comprise helical threading of a second direction opposite the first direction.

During surgery, and after device 100 containing expansion mechanisms 106 is implanted in situ within disc space 12, a surgeon can apply torque to threaded rod 116 via any device that imparts rotational force (e.g., a screw driver or impact driver). As threaded rod 116 rotates in first rotational direction RO1, second fixed collar 138 maintains a fixed axial position about threaded rod 116 as it is confined by locking mechanism 148. Additionally, as threaded rod 116 rotates in first rotational direction RO1, the inner circumferential threading of second threaded collar 136 engages with the helical threading of threaded rod 116 causing second threaded collar 136 to translate in second axial direction AD2. The translational motion imparted to second threaded collar 136, in conjunction with the lack of translational motion of second fixed collar 138, imparts a force upon third strut 142 and fourth strut 146 which in turn impart a force upon third arm 140 and fourth arm 144 in first radial direction RD1 and second radial direction RD2, respectively.

First arm 126, second arm 130, third arm 140, and fourth arm 144, contain a recess, i.e., first recess 150, second recess 152, third recess 154, and fourth recess 156, respectively. When expansion mechanism 106 is in a collapsed state as illustrated in FIG. 15, first recess 150 of first arm 126 is arranged to receive first strut 128 such that first strut 128 is completely nested within first recess 150. Similarly, second recess 152, third recess 154, and fourth recess 156 are arranged to receive second strut 132, third strut 142, and fourth strut 146, respectively, such that each strut is completely nested within a respective recess. Alternatively, each strut could contain a recess arranged to receive each arm such that each arm is nested completely within the recess of each respective strut.

Figure 17:
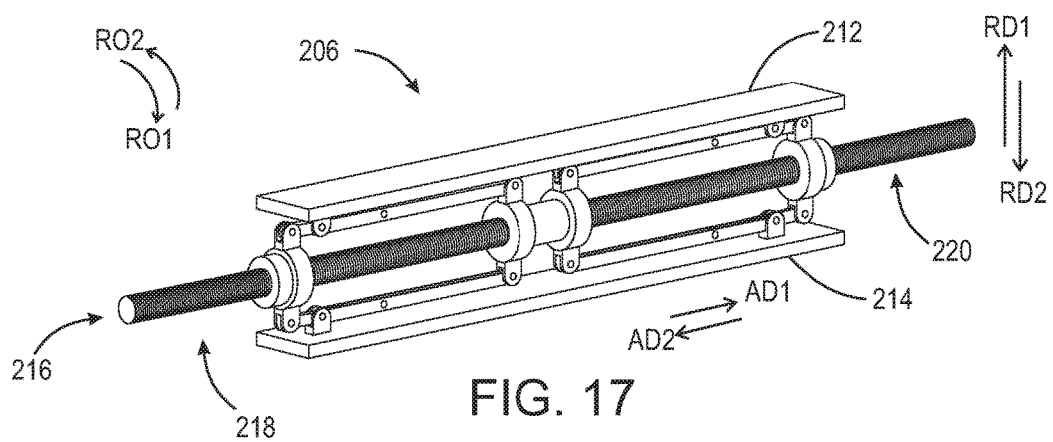
FIG. 17 is a perspective view of a second example embodiment of an expansion mechanism in a collapsed state.
Figure 18:
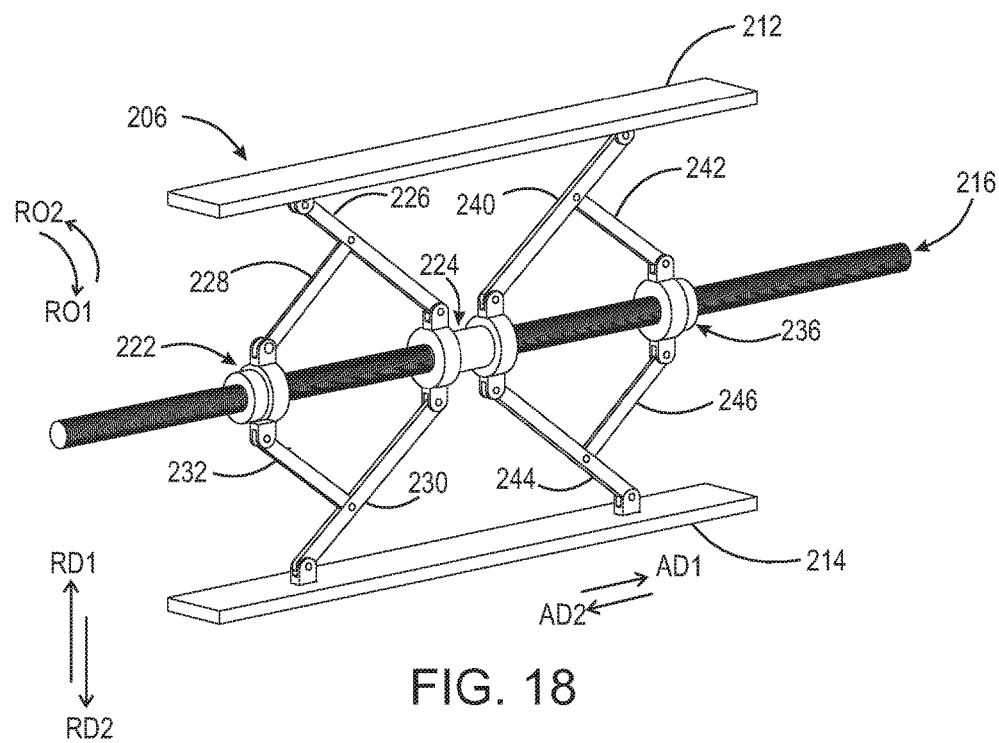
FIG. 18 is a perspective view of a second example embodiment of an expansion mechanism in an expanded state.

FIGS. 17 and 18 illustrate perspective views of expansion mechanism 206 in a collapsed and expanded state, respectively. Expansion mechanism 206 includes superior plate 212, inferior plate 214, threaded rod 216 having first end 218 and second end 220, first threaded collar 222, fixed collar 224, first arm 226, first strut 228, second arm 230, second strut 232, and locking mechanism 234 (not shown). Superior plate 212 and inferior plate 214 are substantially planar members spanning a substantial portion of the length of a device when in place therein, e.g., device 100. Superior plate 212 and inferior plate 214 are arranged to contact and engage with the inner surface of superior component 102 and inferior component 104 of device 100, respectively. Threaded rod 216 is arranged to run along the length of device 100 and to rotate within device 100 in either first rotational direction RO1 or second rotational direction RO2. Threaded rod 216 has an outer circumferential surface which contains helical threading. The helical threading can be threaded in first rotational direction RO1 and/or second rotational direction RO2.

First threaded collar 222 is a substantially toroidal member with inner threading operatively arranged to receive and engage with the helical threading on first end 218 of threaded rod 216. As threaded rod 216 is rotated in first rotational direction RO1 or second rotational direction RO2, the first threaded collar 222 translates about threaded rod 216 in first axial direction AD1 or second axial direction AD2, dependent on the direction of rotation of threaded rod 216. Fixed collar 224 is a substantially toroidal member arranged about threaded rod 216 and arranged to rotate freely in place and maintain position in first axial direction AD1. This free rotation can be accomplished by leaving the inner circumferential surface of fixed collar 224 free of threading, such that the threading of threaded rod 216 cannot engage with and influence fixed collar 224. Additionally, a locking mechanism, i.e., locking mechanism 234 (not shown), discussed infra, can be used to prevent fixed collar 224 from translating about threaded rod 216 in first axial direction AD1 and/or second axial direction AD2. Alternatively, and although not illustrated in the figures, the inner circumferential surface of fixed collar 224 can contain an annular protrusion arranged to fit within and slidingly engage with a corresponding annular recess at a fixed axial position on the outer circumferential surface of threaded rod 216.

First arm 226 is pivotably connected between fixed collar 224 and superior plate 212. One end of first arm 226 is pivotably connected to a protrusion on the inner surface of superior plate 212 which can comprise a pin arranged to allow first arm 226 to pivot with respect to superior plate 212. The other end of first arm 226 is pivotably connected to a first protrusion on the outer circumferential surface of fixed collar 224 which can comprise a pin arranged to allow first arm 226 to pivot with respect to fixed collar 224. First strut 228 is pivotably connected between first threaded collar 222 and first arm 226. One end of first strut 228 is pivotably connected to a protrusion on the outer circumferential surface of first threaded collar 222 which can comprise a pin arranged to allow first strut 228 to pivot with respect to first threaded collar 222. The other end of first strut 228 is pivotably connected to first arm 226 which can comprise a pin arranged to allow first strut 228 to pivot with respect to first arm 226.

Second arm 230 is pivotably connected between fixed collar 224 and inferior plate 214. One end of second arm 230 is pivotably connected to a protrusion on the inner surface of inferior plate 214 which can comprise a pin arranged to allow second arm 230 to pivot with respect to inferior plate 214. The other end of second arm 230 is pivotably connected to a second protrusion on the outer circumferential surface of fixed collar 224 which can comprise a pin arranged to allow second arm 230 to pivot with respect to fixed collar 224. Second strut 232 is pivotably connected between first threaded collar 222 and second arm 230. One end of second strut 232 is pivotably connected to a second protrusion on the outer circumferential surface of first threaded collar 222 which can comprise a pin arranged to allow second strut 232 to pivot with respect to first threaded collar 222. The other end of second strut 232 is pivotably connected to second arm 230 which can comprise a pin arranged to allow second strut 232 to pivot with respect to second arm 230.

Expansion mechanism 206 also includes second threaded collar 236, third arm 240, third strut 242, fourth arm 244, and fourth strut 246. Second threaded collar 236 is a substantially toroidal member with inner threading operatively arranged to receive and engage with the helical threading on second end 220 of threaded rod 216. As threaded rod 216 is rotated in first rotational direction RO1 or second rotational direction RO2, second threaded collar 236 translates about threaded rod 216 in first axial direction AD1 or second axial direction AD2 dependent on the direction of rotation of threaded rod 216.

Third arm 240 is pivotably connected between fixed collar 224 and superior plate 212. One end of third arm 240 is pivotably connected to a protrusion on the inner surface of superior plate 212 which can comprise a pin arranged to allow third arm 240 to pivot with respect to superior plate 212. The other end of third arm 240 is pivotably connected to a third protrusion on the outer circumferential surface of fixed collar 224 which can comprise a pin arranged to allow third arm 240 to pivot with respect to fixed collar 224. Third strut 242 is pivotably connected between second threaded collar 236 and third arm 240. One end of third strut 242 is pivotably connected to a protrusion on the outer circumferential surface of second threaded collar 236 which can comprise a pin arranged to allow third strut 242 to pivot with respect to second threaded collar 236. The other end of third strut 242 is pivotably connected to third arm 240 which can comprise a pin arranged to allow third strut 242 to pivot with respect to third arm 240.

Fourth arm 244 is pivotably connected between fixed collar 224 and inferior plate 214. One end of fourth arm 244 is pivotably connected to a protrusion on the inner surface of inferior plate 214 which can comprise a pin arranged to allow fourth arm 244 to pivot with respect to inferior plate 214. The other end of fourth arm 244 is pivotably connected to a fourth protrusion on the outer circumferential surface of fixed collar 224 which can comprise a pin arranged to allow fourth arm 244 to pivot with respect to fixed collar 224. Fourth strut 246 is pivotably connected between second threaded collar 236 and fourth arm 244. One end of fourth strut 246 is pivotably connected to a second protrusion on the outer circumferential surface of second threaded collar 236 which can comprise a pin arranged to allow fourth strut 246 to pivot with respect to second threaded collar 236. The other end of fourth strut 246 is pivotably connected to fourth arm 244 which can comprise a pin arranged to allow fourth strut 246 to pivot with respect to fourth arm 244.

Locking mechanism 234 (not shown) can be arranged about threaded rod 216 and be positioned axially adjacent to fixed collar 224 in the first axial direction AD1 and/or the second axial direction AD2. As fixed collar 224 does not have internal threading, locking mechanism 234 prevents fixed collar 224 from translating about threaded rod 216 in first axial direction AD1 and/or second axial direction AD2. In an example embodiment, locking mechanism 234 is a lock washer, a crimp ring retainer, or a serrated lock washer. However, it should be appreciated that locking mechanism 234 can be any mechanism suitable for preventing axial translation about a cylindrical rod.

During surgery, and after device 100 containing expansion mechanisms 206 is implanted in situ within disc space 12, a surgeon can apply torque to threaded rod 216 via any device that imparts rotational force (e.g., a screw driver or impact driver). As threaded rod 216 rotates in first rotational direction RO1, fixed collar 224 maintains a fixed axial position about threaded rod 216 as it is confined by locking mechanism(s) 234. Additionally, as threaded rod 216 rotates in first rotational direction RO1, the inner circumferential threading of first threaded collar 222 and second threaded collar 236 engages with the helical threading of threaded rod 216 causing first threaded collar 222 and second threaded collar 236 to translate in first axial direction AD1 and second axial direction AD2, respectively. The translational motion imparted to first threaded collar 222 and second threaded collar 236, in conjunction with the lack of translational motion of fixed collar 224, imparts a force upon first strut 228, second strut 232, third strut 242, and fourth strut 246, which in turn impart a force upon first arm 226, second arm 230, third arm 240, and fourth arm 244, displacing superior plate 212 and inferior plate 214 in first radial direction RD1 and second radial direction RD2, respectively.

Although not illustrated, first arm 226, second arm 230, third arm 240, and fourth arm 244, contain a recess, i.e., first recess 250, second recess 252, third recess 254, and fourth recess 256, respectively. When expansion mechanism 206 is in a collapsed state as illustrated in FIG. 17, first recess 250 of first arm 226 is arranged to receive first strut 228 such that first strut 228 is completely nested within first recess 250. Similarly, second recess 252, third recess 254, and fourth recess 256 are arranged to receive second strut 232, third strut 242, and fourth strut 246, respectively, such that each strut is completely nested within a respective recess. Alternatively, each strut could contain a recess arranged to receive each arm such that each arm is nested completely within the recess of each respective strut.

Figure 19:
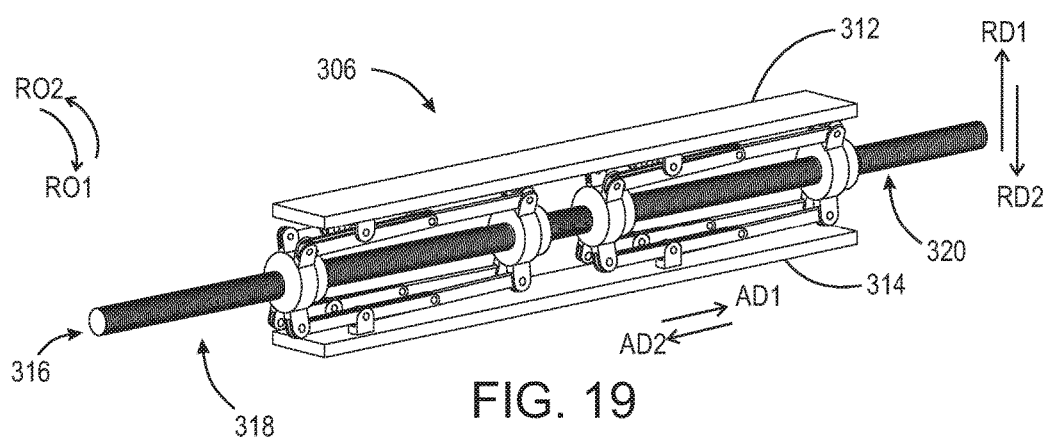
FIG. 19 is a perspective view of a third example embodiment of an expansion mechanism in a collapsed state.
Figure 20:
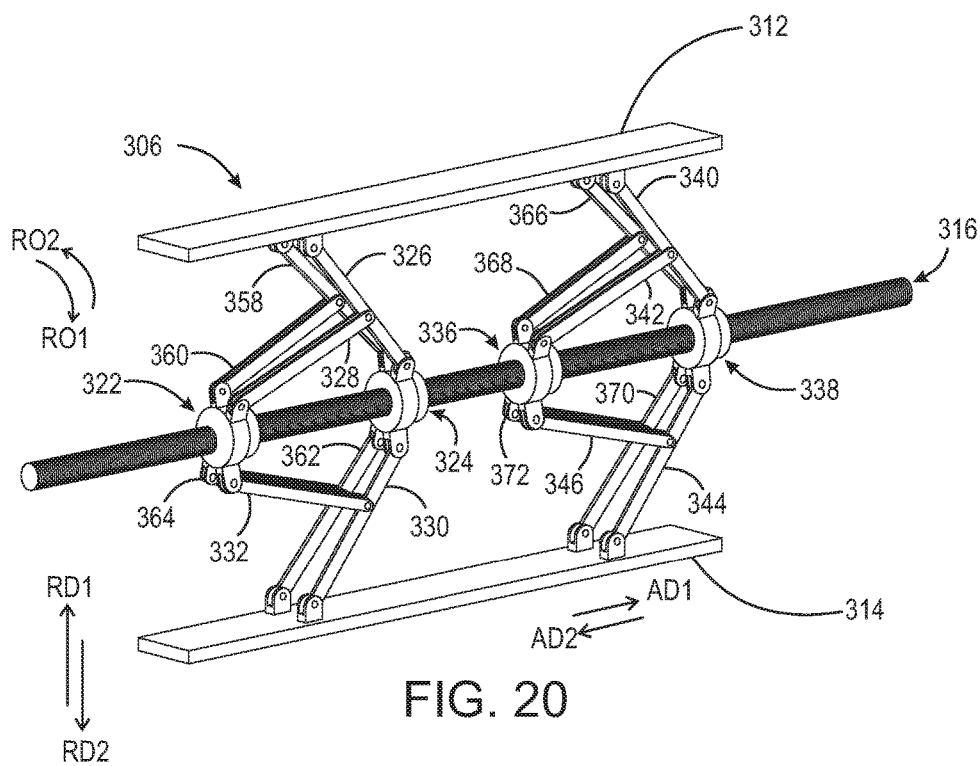
FIG. 20 is a perspective view of a third example embodiment of an expansion mechanism in an expanded state.

FIGS. 19 and 20 illustrate perspective views of expansion mechanism 306 in a collapsed and an expanded state, respectively. Expansion mechanism 306 includes superior plate 312, inferior plate 314, threaded rod 316 having first end 318 and second end 320, first threaded collar 322, first fixed collar 324, first arm 326, first strut 328, second arm 330, second strut 332, fifth arm 358, fifth strut 360, sixth arm 362, sixth strut 364, and locking mechanism 33 (not shown). Superior plate 312 and inferior plate 314 are substantially planar members spanning a substantial portion of the length of a device, e.g., device 100. Superior plate 312 and inferior plate 314 are arranged to contact and engage with the inner surface of superior component 102 and inferior component 104 of device 100, respectively. Threaded rod 316 is arranged to run along the length of device 100 and to rotate within device 100 in either first rotational direction RO1 or second rotational direction RO2. Threaded rod 316 has an outer circumferential surface which contains helical threading. The helical threading can be threaded in first rotational direction RO1 and/or second rotational direction RO2.

First threaded collar 322 is a substantially toroidal member with inner threading operatively arranged to receive and engage with the helical threading on first end 318 of threaded rod 316. As threaded rod 316 is rotated in first rotational direction RO1 or second rotational direction RO2, the first threaded collar 322 translates about threaded rod 316 in first axial direction AD1 or second axial direction AD2, dependent on the direction of rotation of threaded rod 316. First fixed collar 324 is a substantially toroidal member arranged about threaded rod 316 and arranged to rotate freely in place and maintain position in first axial direction AD1. This free rotation can be accomplished by leaving the inner circumferential surface of first fixed collar 324 free of threading, such that the threading of threaded rod 316 cannot engage with and influence first fixed collar 324. Additionally, a locking mechanism, i.e., locking mechanism 334 (not shown), discussed infra, can be used to prevent first fixed collar 324 from translating about threaded rod 316 in first axial direction AD1 and/or second axial direction AD2. Alternatively, and although not illustrated in the figures, the inner circumferential surface of first fixed collar 324 can contain an annular protrusion arranged to fit within and slidingly engage with a corresponding annular recess at a fixed axial position on the outer circumferential surface of threaded rod 316.

First arm 326 is pivotably connected between first fixed collar 324 and superior plate 312. One end of first arm 326 is pivotably connected to a protrusion on the inner surface of superior plate 312 which can comprise a pin arranged to allow first arm 326 to pivot with respect to superior plate 312. The other end of first arm 326 is pivotably connected to a protrusion on the outer circumferential surface of first fixed collar 324 which can comprise a pin arranged to allow first arm 326 to pivot with respect to first fixed collar 324. First strut 328 is pivotably connected between first threaded collar 322 and first arm 326. One end of first strut 328 is pivotably connected to a protrusion on the outer circumferential surface of first threaded collar 322 which can comprise a pin arranged to allow first strut 328 to pivot with respect to first threaded collar 322. The other end of first strut 328 is pivotably connected to first arm 326 which can comprise a pin arranged to allow first strut 328 to pivot with respect to first arm 326.

Second arm 330 is pivotably connected between first fixed collar 324 and inferior plate 314. One end of second arm 330 is pivotably connected to a protrusion on the inner surface of inferior plate 314 which can comprise a pin arranged to allow second arm 330 to pivot with respect to inferior plate 314. The other end of second arm 330 is pivotably connected to a second protrusion on the outer circumferential surface of first fixed collar 324 which can comprise a pin arranged to allow second arm 330 to pivot with respect to first fixed collar 324. Second strut 332 is pivotably connected between first threaded collar 322 and second arm 330. One end of second strut 332 is pivotably connected to a second protrusion on the outer circumferential surface of first threaded collar 322 which can comprise a pin arranged to allow second strut 332 to pivot with respect to first threaded collar 322. The other end of second strut 332 is pivotably connected to second arm 330 which can comprise a pin arranged to allow second strut 332 to pivot with respect to second arm 330.

Fifth arm 358 is pivotably connected between first fixed collar 324 and superior plate 312. One end of fifth arm 358 is pivotably connected to a protrusion on the inner surface of superior plate 312 which can comprise a pin arranged to allow fifth arm 358 to pivot with respect to superior plate 312. The other end of fifth arm 358 is pivotably connected to a third protrusion on the outer circumferential surface of first fixed collar 324 which can comprise a pin arranged to allow fifth arm 358 to pivot with respect to first fixed collar 324. Fifth strut 360 is pivotably connected between first threaded collar 322 and fifth arm 358. One end of fifth strut 360 is pivotably connected to a third protrusion on the outer circumferential surface of first threaded collar 322 which can comprise a pin arranged to allow fifth strut 360 to pivot with respect to first threaded collar 322. The other end of fifth strut 360 is pivotably connected to fifth arm 358 which can comprise a pin arranged to allow fifth strut 360 to pivot with respect to fifth arm 358.

Sixth arm 362 is pivotably connected between first fixed collar 324 and inferior plate 314. One end of sixth arm 362 is pivotably connected to a protrusion on the inner surface of inferior plate 314 which can comprise a pin arranged to allow sixth arm 362 to pivot with respect to inferior plate 314. The other end of sixth arm 362 is pivotably connected to a fourth protrusion on the outer circumferential surface of first fixed collar 324 which can comprise a pin arranged to allow sixth arm 362 to pivot with respect to first fixed collar 324. Sixth strut 364 is pivotably connected between first threaded collar 322 and sixth arm 362. One end of sixth strut 364 is pivotably connected to a fourth protrusion on the outer circumferential surface of first threaded collar 322 which can comprise a pin arranged to allow sixth strut 364 to pivot with respect to first threaded collar 322. The other end of sixth strut 364 is pivotably connected to sixth arm 362 which can comprise a pin arranged to allow sixth strut 364 to pivot with respect to sixth arm 362.

Locking mechanism 334 (not shown) is arranged about threaded rod 316 and be positioned axially adjacent to first fixed collar 324 in the first axial direction AD1 and/or the second axial direction AD2. As first fixed collar 324 does not have internal threading, locking mechanism 334 prevents first fixed collar 324 from translating about threaded rod 316 in first axial direction AD1 and/or second axial direction AD2. In an example embodiment, locking mechanism 334 is a lock washer, a crimp ring retainer, or a serrated lock washer. However, it should be appreciated that locking mechanism 334 can be any mechanism suitable for preventing axial translation about a cylindrical rod.

During surgery, and after device 100 containing expansion mechanisms 306 is implanted in situ within disc space 12, a surgeon can apply torque to threaded rod 316 via any device that imparts rotational force (e.g., a screw driver or impact driver). As threaded rod 316 rotates in first rotational direction RO1, first fixed collar 324 maintains a fixed axial position about threaded rod 316 as it is confined by locking mechanism 334. Additionally, as threaded rod 316 rotates in first rotational direction RO1, the inner circumferential threading of first threaded collar 322 engages with the helical threading of threaded rod 316 causing first threaded collar 322 to translate in first axial direction AD1. The translational motion imparted to first threaded collar 322, in conjunction with the lack of translational motion of first fixed collar 324, imparts a force upon first strut 328, second strut 332, fifth strut 360, and sixth strut 364, which in turn impart a force upon first arm 326 and fifth arm 358 in first radial direction RD1, and second arm 330 and sixth arm 362 in second radial direction RD2.

Expansion mechanism 306 also includes second threaded collar 336, second fixed collar 338, third arm 340, third strut 342, fourth arm 344, fourth strut 346, seventh arm 366, seventh strut 368, eight arm 370, eight strut 372, and locking mechanism 348 (not shown). Second threaded collar 336 is a substantially toroidal member with inner threading operatively arranged to receive and engage with the helical threading on second end 320 of threaded rod 316. As threaded rod 316 is rotated in first rotational direction RO1 or second rotational direction RO2, second threaded collar 336 translates about threaded rod 316 in first axial direction AD1 or second axial direction AD2, dependent on the direction of rotation of threaded rod 316. Second fixed collar 338 is a substantially toroidal member arranged about threaded rod 316 and arranged to rotate freely in place and maintain position in first axial direction AD1. This free rotation can be accomplished by leaving the inner circumferential surface of second fixed collar 338 free of threading, such that the threading of threaded rod 316 cannot engage with and influence second fixed collar 338. Additionally, a locking mechanism, i.e., locking mechanism 348 (not shown), discussed infra, can be used to prevent second fixed collar 338 from translating about threaded rod 316 in first axial direction AD1 and/or second axial direction AD2. Alternatively, and although not illustrated in the figures, the inner circumferential surface of second fixed collar 338 can contain an annular protrusion arranged to fit within and slidingly engage with a corresponding annular recess at a fixed axial position on the outer circumferential surface of threaded rod 316.

Third arm 340 is pivotably connected between second fixed collar 338 and superior plate 312. One end of third arm 340 is pivotably connected to a protrusion on the inner surface of superior plate 312 which can comprise a pin arranged to allow third arm 340 to pivot with respect to superior plate 312. The other end of third arm 340 is pivotably connected to a protrusion on the outer circumferential surface of second fixed collar 338 which can comprise a pin arranged to allow third arm 340 to pivot with respect to second fixed collar 338. Third strut 342 is pivotably connected between second threaded collar 336 and third arm 340. One end of third strut 342 is pivotably connected to a protrusion on the outer circumferential surface of second threaded collar 336 which can comprise a pin arranged to allow third strut 342 to pivot with respect to second threaded collar 336. The other end of third strut 342 is pivotably connected to third arm 340 which can comprise a pin arranged to allow third strut 342 to pivot with respect to third arm 340.

Fourth arm 344 is pivotably connected between second fixed collar 338 and inferior plate 314. One end of fourth arm 344 is pivotably connected to a protrusion on the inner surface of inferior plate 314 which can comprise a pin arranged to allow fourth arm 344 to pivot with respect to inferior plate 314. The other end of fourth arm 344 is pivotably connected to a second protrusion on the outer circumferential surface of second fixed collar 338 which can comprise a pin arranged to allow fourth arm 344 to pivot with respect to second fixed collar 338. Fourth strut 346 is pivotably connected between second threaded collar 336 and fourth arm 344. One end of fourth strut 346 is pivotably connected to a second protrusion on the outer circumferential surface of second threaded collar 336 which can comprise a pin arranged to allow fourth strut 346 to pivot with respect to second threaded collar 336. The other end of fourth strut 346 is pivotably connected to fourth arm 344 which can comprise a pin arranged to allow fourth strut 346 to pivot with respect to fourth arm 344.

Seventh arm 366 is pivotably connected between second fixed collar 338 and superior plate 312. One end of seventh arm 366 is pivotably connected to a protrusion on the inner surface of superior plate 312 which can comprise a pin arranged to allow seventh arm 366 to pivot with respect to superior plate 312. The other end of seventh arm 366 is pivotably connected to a third protrusion on the outer circumferential surface of second fixed collar 338 which can comprise a pin arranged to allow seventh arm 366 to pivot with respect to second fixed collar 338. Seventh strut 368 is pivotably connected between second threaded collar 336 and seventh arm 366. One end of seventh strut 368 is pivotably connected to a third protrusion on the outer circumferential surface of second threaded collar 336 which can comprise a pin arranged to allow seventh strut 368 to pivot with respect to second threaded collar 336. The other end of seventh strut 368 is pivotably connected to seventh arm 366 which can comprise a pin arranged to allow seventh strut 368 to pivot with respect to seventh arm 366.

Eighth arm 370 is pivotably connected between second fixed collar 338 and inferior plate 314. One end of eighth arm 370 is pivotably connected to a protrusion on the inner surface of inferior plate 314 which can comprise a pin arranged to allow eighth arm 370 to pivot with respect to inferior plate 314. The other end of eighth arm 370 is pivotably connected to a fourth protrusion on the outer circumferential surface of second fixed collar 338 which can comprise a pin arranged to allow eighth arm 370 to pivot with respect to second fixed collar 338. Eighth strut 372 is pivotably connected between second threaded collar 336 and eighth arm 370. One end of eighth strut 372 is pivotably connected to a fourth protrusion on the outer circumferential surface of second threaded collar 336 which can comprise a pin arranged to allow eighth strut 372 to pivot with respect to second threaded collar 336. The other end of eighth strut 372 is pivotably connected to eighth arm 370 which can comprise a pin arranged to allow eighth strut 372 to pivot with respect to eighth arm 370.

Locking mechanism 348 (not shown) can be arranged about threaded rod 316 and be positioned axially adjacent to second fixed collar 338 in the first axial direction AD1 and/or the second axial direction AD2. As second fixed collar 338 does not have internal threading, locking mechanism 348 prevents second fixed collar 338 from translating about threaded rod 316 in first axial direction AD1 and/or second axial direction AD2. In an example embodiment, locking mechanism 348 is a lock washer, a crimp ring retainer, or a serrated lock washer. However, it should be appreciated that locking mechanism 348 can be any mechanism suitable for preventing axial translation about a rod. It should be appreciated that although first threaded collar 322 and second threaded collar 336 are positioned such that each translates in the same axial direction, they could be positioned such that they each translate in opposing directions. The opposing movement of first threaded collar 322 and second threaded collar 336 could be achieved by having opposing threading on their respective inner circumferential surfaces, or the threaded collars could have identical threading and first end 318 of threaded rod 316 could comprise helical threading of a first direction while second end 320 of threaded rod 316 could comprise helical threading of a second direction opposite the first direction.

During surgery, and after device 100 containing expansion mechanisms 306 is implanted in situ within disc space 12, a surgeon can apply torque to threaded rod 316 via any device that imparts rotational force (e.g., a screw driver or impact driver). As threaded rod 316 rotates in first rotational direction RO1, second fixed collar 338 maintains a fixed axial position about threaded rod 316 as it is confined by locking mechanism 348. Additionally, as threaded rod 316 rotates in first rotational direction RO1, the inner circumferential threading of second threaded collar 336 engages with the helical threading of threaded rod 316 causing second threaded collar 336 to translate in first axial direction AD1. The translational motion imparted to second threaded collar 336, in conjunction with the lack of translational motion of second fixed collar 338, imparts a force upon third strut 342, fourth strut 346, seventh strut 368, and eighth strut 372, which in turn impart a force upon third arm 340 and seventh arm 366 in first radial direction RD1, and fourth arm 344 and eighth arm 370 in second radial direction RD2.

Although not illustrated, First arm 326, second arm 330, third arm 340, fourth arm 344, fifth arm 358, sixth arm 362, seventh arm 366, and eighth arm 370, each contain a recess, i.e., first recess 350, second recess 352, third recess 354, fourth recess 356, fifth recess 374, sixth recess 376, seventh recess 378, and eight recess 380, respectively. When expansion mechanism 306 is in a collapsed state as illustrated in FIG. 19, first recess 350 of first arm 326 is arranged to receive first strut 328 such that first strut 328 is completely nested within first recess 350. Similarly, second recess 152, third recess 154, fourth recess 156, fifth recess 374, sixth recess 376, seventh recess 378, and eight recess 380, are all arranged to receive second strut 332, third strut 342, fourth strut 346, fifth strut 360, sixth strut 364, seventh strut 368, and eighth strut 372 respectively, such that each strut is completely nested within a respective recess. Alternatively, each strut could contain a recess arranged to receive each arm such that each arm is nested completely within the recess of each respective strut.

Thus it is seen that the objects of the invention are efficiently obtained, although changes and modifications to the invention should be readily apparent to those having ordinary skill in the art, which changes would not depart from the spirit and scope of the invention as claimed.

LIST OF REFERENCE NUMBERS

10 Spinal column
12 Disc space
C1-C7 Cervical vertebrae
T1-T9 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
$H_1$ Collapsed height
$H_2$ Expanded height
SP Spinous process
TP Transverse process
IF Intervertebral foramen
A Annulus
AR Axis of rotation
N Nucleus
NC Neural canal
$H_1$ Unexpanded height
$H_2$ Expanded height
RD1 Rotational direction
RD2 Rotational direction
AD1 Axial direction
AD2 Axial direction
RO1 Radial direction
RO2 Radial direction
100 Device
102 Superior component
104 Inferior component
106 Expansion mechanism
108 First aperture
110 Second aperture
112 Superior plate
114 Inferior plate
116 Threaded rod
118 First end
120 Second end
122 First threaded collar
124 First fixed collar
126 First arm
128 First strut
130 Second arm
132 Second strut
134 Locking mechanism
136 Second threaded collar
138 Second fixed collar
140 Third arm
142 Third strut
144 Fourth arm
146 Fourth strut
148 Locking mechanism
150 First recess
152 Second recess
154 Third recess
156 Fourth recess
206 Expansion mechanism
212 Superior plate
214 Inferior plate
216 Threaded rod
218 First end
220 Second end
222 First threaded collar
224 Fixed collar
226 First arm
228 First strut
230 Second arm
232 Second strut
234 Locking mechanism
236 Second threaded collar
240 Third arm
242 Third strut
244 Fourth arm
246 Fourth strut
250 First recess
252 Second recess
254 Third recess
256 Fourth recess
306 Expansion mechanism
312 Superior plate
314 Inferior plate
316 Threaded rod
318 First end
320 Second end
322 First threaded collar
324 First fixed collar
326 First arm
328 First strut 330 Second arm
332 Second strut
334 Locking mechanism
336 Second threaded collar
338 Second fixed collar
340 Third arm
342 Third strut
344 Fourth arm
346 Fourth strut
348 Locking mechanism
350 First recess
352 Second recess
354 Third recess
356 Fourth recess
358 Fifth arm
360 Fifth strut
362 Sixth arm
364 Sixth strut
366 Seventh arm
368 Seventh strut
370 Eighth arm
372 Eighth strut
374 Fifth recess
376 Sixth recess
378 Seventh recess
380 Eighth recess

What is claimed is:

1. An expandable interbody spinal fusion device, comprising:
   a superior component;
   an inferior component;
   an expansion mechanism comprising:
      a threaded rod;
      a threaded collar operatively arranged to engage with the threaded rod and axially translate in a first axial direction;
      a fixed collar secured about the threaded rod;
      a first arm including a first end and a second end, the first end pivotably secured to the fixed collar; and,
      a first strut pivotably secured to:
         the first arm at a point intermediate the first and second ends; and,
         the threaded collar.

2. The expandable interbody spinal fusion device of claim 1 wherein the first arm is pivotably secured to a superior plate.

3. The expandable interbody spinal fusion device of claim 1 wherein the expansion mechanism further comprises:
   a second arm pivotably secured to an inferior plate and the fixed collar; and,
   a second strut pivotably secured to the second arm and the threaded collar.

4. The expandable interbody spinal fusion device of claim 3 wherein the expansion mechanism further comprises:
   a superior plate arranged to pivotably connect with the first arm, wherein the threaded rod is rotated in a first rotational direction to displace the superior plate in a first direction orthogonal an axis of rotation of the threaded rod, and displace the inferior plate in a second direction orthogonal to the axis of rotation and opposite the first direction.

5. The expandable interbody spinal fusion device of claim 4 wherein the superior plate has a first surface arranged to contact and displace the superior component, and the inferior plate has a first surface arranged to contact and displace the inferior component.

6. The expandable interbody spinal fusion device of claim 1 wherein the first arm comprises a first recess operatively arranged to receive the first strut when the expandable interbody spinal fusion device is in a collapsed state.

7. The expandable interbody spinal fusion device of claim 6 wherein the second arm comprises a second recess operatively arranged to receive the second strut when the expandable interbody spinal fusion device is in a collapsed state.

8. The expandable interbody spinal fusion device of claim 1 wherein a locking mechanism is positioned on the threaded rod adjacent to the fixed collar in the first direction or second direction such that the fixed collar is prevented from being displaced in the first direction or second direction, respectively.

9. The expandable interbody spinal fusion device of claim 8 wherein the locking mechanism is a lock washer, a crimp ring retainer, or a serrated lock washer.

10. An expandable interbody spinal fusion device, comprising:
    a superior component;
    an inferior component;
    a first expansion mechanism comprising:
       a threaded rod;
       a superior plate;
       an inferior plate;
       a first threaded collar operatively arranged to engage with the threaded rod;
       a first fixed collar fixedly arranged about the threaded rod;
       a first arm pivotably secured to the superior plate and the first fixed collar, the first arm comprising a first recess;
       a first strut pivotably secured to the first arm and the first threaded collar, the first recess operatively arranged to receive the first strut;
       a second arm pivotably secured to the inferior plate and the first fixed collar, the second arm comprising a second recess; and,
       a second strut pivotably secured to the second arm and the first threaded collar the second recess operatively arranged to receive the second strut,
       wherein the threaded rod is rotated about a first axis of rotation in a first rotational direction to displace the superior component in a first direction orthogonal to the first axis of rotation.

11. The expandable interbody spinal fusion device of claim 10 wherein the first expansion mechanism further comprises:
    a second threaded collar operatively arranged to engage with the threaded rod;
    a second fixed collar arranged about the threaded rod;
    a third arm pivotably secured to the superior plate and the second fixed collar;
    a third strut pivotably secured to the third arm and the second threaded collar;
    a fourth arm pivotably secured to the inferior plate and the second fixed collar; and,
    a fourth strut pivotably secured to the fourth arm and the second threaded collar.

12. The expandable interbody spinal fusion device of claim 11 wherein the third arm comprises a third recess operatively arranged to receive the third strut, the fourth arm comprises a fourth recess operatively arranged to receive the fourth strut.

13. The expandable interbody spinal fusion device of claim 10 wherein a locking mechanism is positioned on the threaded rod adjacent to the first fixed collar and the second fixed collar such that the first fixed collar is prevented from being displaced in a first axial direction and the second fixed collar is prevented from being displaced in a second axial direction opposite the first axial direction.

14. The expandable interbody spinal fusion device of claim 13 wherein the locking mechanism is a lock washer, crimp ring retainer, or a serrated lock washer.

15. An expandable interbody spinal fusion device, comprising:
    a superior component;
    an inferior component; and,
    an expansion mechanism comprising:
        a superior plate;
        an inferior plate;
        a threaded rod;
        a first threaded collar operatively arranged to engage with the threaded rod;
        a second threaded collar operatively arranged to engage with the threaded rod;
        a fixed collar arranged about the threaded rod;
        a first arm pivotably secured to the superior plate and the fixed collar;
        a first strut pivotably secured to the first arm and the first threaded collar;
        a second arm pivotably secured to the inferior plate and the fixed collar;
        a second strut pivotably secured to the second arm and the first threaded collar;
        a third arm pivotably secured to the superior plate and the fixed collar;
        a third strut pivotably secured to the third arm and the second threaded collar;
        a fourth arm pivotably secured to the inferior plate and the fixed collar; and,
        a fourth strut pivotably secured to the fourth arm and the second threaded collar,
        wherein the threaded rod is rotated in a first rotational direction about an axis of rotation to displace the first threaded collar in a first axial direction and displace the second threaded collar in a second axial direction, and displacing the superior component in a first radial direction orthogonal to the first axial direction, and displace the inferior component in a second radial direction orthogonal to the first axial direction and opposite the first radial direction.

16. An expandable interbody spinal fusion device of claim 15 wherein the threaded rod has a first end and a second end, the first end threaded in a first rotational direction and the second end of the threaded rod is threaded in a second rotational direction.

17. The expandable interbody spinal fusion device of claim 15 wherein the first arm further comprises a first recess operatively arranged to receive the first strut when the expandable interbody spinal fusion device is in a collapsed state, and the second arm further comprises a second recess operatively arranged to receive the second strut when the expandable interbody spinal fusion device is in a collapsed state.

18. The expandable interbody spinal fusion device of claim 17 wherein the third arm further comprises a third recess operatively arranged to receive the third strut when the expandable interbody spinal fusion device is in a collapsed state, and the fourth arm further comprises a fourth recess operatively arranged to receive the fourth strut when the expandable interbody spinal fusion device is in a collapsed state.

19. The expandable interbody spinal fusion device of claim 15 wherein a locking mechanism is positioned on the threaded rod adjacent to the fixed collar in the first axial direction and the second axial direction such that the fixed collar is prevented from being displaced in the first axial direction and the second axial direction.

20. The expandable interbody spinal fusion device of claim 19 wherein the locking mechanism is a lock washer, crimp ring retainer, or a serrated lock washer.

* * * * *